(12) United States Patent
Lei

(10) Patent No.: US 6,511,699 B1
(45) Date of Patent: Jan. 28, 2003

(54) ENZYMES WITH IMPROVED PHYTASE ACTIVITY

(75) Inventor: Xingen Lei, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/540,149

(22) Filed: Mar. 31, 2000

Related U.S. Application Data

(60) Provisional application No. 60/127,032, filed on Mar. 31, 1999.

(51) Int. Cl.[7] .............................. A23L 1/20; A23K 1/00; C12N 9/16; C07K 1/00

(52) U.S. Cl. ..................... 426/630; 530/350; 435/252.3; 435/320.1; 435/196; 426/635

(58) Field of Search ............................ 435/196, 252.3, 435/320.1, 254.2, 254.23, 254.21; 530/350; 426/656, 630, 635

(56) References Cited

U.S. PATENT DOCUMENTS

| | | | |
|---|---|---|---|
| 3,819,528 A | 6/1974 | Berry | 252/153 |
| 3,860,484 A | 1/1975 | O'Malley | 195/63 |
| 3,966,971 A | 6/1976 | Morehouse et al. | 426/44 |
| 4,038,140 A | 7/1977 | Jaworek et al. | 195/63 |
| 4,375,514 A | 3/1983 | Siewert et al. | 435/172 |
| 4,460,683 A | 7/1984 | Gloger et al. | 435/10 |
| 4,470,968 A | 9/1984 | Mitra et al. | 424/101 |
| 4,734,283 A | 3/1988 | Sirén | 424/439 |
| 4,765,994 A | 8/1988 | Holmgren | 426/31 |
| 4,778,761 A | 10/1988 | Miyanohara et al. | 435/320 |
| 4,914,029 A | 4/1990 | Caransa et al. | 435/101 |
| 4,915,960 A | 4/1990 | Holmgren | 426/31 |
| 4,950,609 A | 8/1990 | Tischer et al. | 435/18 |
| 4,997,767 A | 3/1991 | Nozaki et al. | 435/320.1 |
| 5,024,941 A | 6/1991 | Maine et al. | 435/69.9 |
| 5,200,399 A | 4/1993 | Wettlaufer et al. | 514/23 |
| 5,268,273 A | 12/1993 | Buckholz | 435/69.1 |
| 5,290,765 A | 3/1994 | Wettlaufer et al. | 514/23 |
| 5,316,770 A | 5/1994 | Edwards, Jr. | 424/442 |
| 5,318,903 A | 6/1994 | Bewert et al. | 435/187 |
| 5,366,736 A | 11/1994 | Edwards, Jr. | 424/442 |
| 5,436,156 A | 7/1995 | VanGorcom et al. | 435/252.3 |
| 5,443,979 A | 8/1995 | Vanderbeke et al. | 435/196 |
| 5,480,790 A | 1/1996 | Tischer et al. | 435/188 |
| 5,492,821 A | 2/1996 | Callstrom et al. | 435/188 |
| 5,516,525 A | 5/1996 | Edwards, Jr. | 424/442 |
| 5,554,399 A | 9/1996 | Vanderbeke et al. | 426/49 |
| 5,556,771 A | 9/1996 | Shen et al. | 435/91.2 |
| 5,612,055 A | 3/1997 | Bedford et al. | 424/442 |
| 5,691,154 A | 11/1997 | Callstrom et al. | 435/7.6 |
| 5,716,655 A | 2/1998 | Hamstra et al. | 426/63 |
| 5,736,625 A | 4/1998 | Callstrom et al. | 530/402 |
| 5,780,292 A | 7/1998 | Nevalainen et al. | 435/256.8 |
| 5,827,709 A | 10/1998 | Barendse et al. | 435/188 |
| 5,830,696 A | 11/1998 | Short | 435/69.1 |
| 5,830,733 A | 11/1998 | Nevalainen et al. | 435/196 |
| 5,834,286 A | 11/1998 | Nevalainen et al. | 435/196 |
| 5,853,779 A | 12/1998 | Takebe et al. | 426/20 |
| 5,863,533 A | 1/1999 | VanGorcom et al. | 424/94.6 |
| 5,876,997 A | 3/1999 | Kretz | 435/196 |
| 5,902,615 A | 5/1999 | Saniez et al. | 426/51 |
| 5,935,624 A | 8/1999 | DeLuca et al. | 426/73 |
| 5,955,448 A | 9/1999 | Colaco et al. | 514/53 |
| 5,972,669 A | 10/1999 | Harz et al. | 435/188 |
| 5,985,605 A | 11/1999 | Cheng et al. | 435/69.1 |
| 5,989,600 A | 11/1999 | Nielsen et al. | 426/52 |
| 6,022,555 A | 2/2000 | DeLuca et al. | 424/442 |
| 6,039,942 A | 3/2000 | Lassen et al. | 424/94.6 |
| 6,063,431 A | 5/2000 | Bae et al. | 426/635 |
| 6,083,541 A | 7/2000 | Hamstra et al. | 426/63 |
| 6,110,719 A | 8/2000 | Kretz | 435/196 |
| 6,139,892 A | 10/2000 | Fredlund et al. | 426/458 |
| 6,139,902 A | 10/2000 | Kondo et al. | 426/656 |
| 6,140,077 A | 10/2000 | Nakamura et al. | 435/69.1 |
| 6,183,740 B1 | 2/2001 | Short et al. | 424/94.6 |
| 6,190,897 B1 | 2/2001 | Kretz | 435/196 |
| 6,204,012 B1 | 3/2001 | Hellmuth et al. | 435/69.1 |
| 6,261,592 B1 | 7/2001 | Nagashima et al. | 424/442 |
| 6,264,946 B1 | 7/2001 | Müllertz et al. | 424/94.2 |
| 6,274,178 B1 | 8/2001 | Beven et al. | 426/54 |
| 6,277,623 B1 | 8/2001 | Oh et al. | 435/252.33 |
| 6,284,502 B1 | 9/2001 | Maenz et al. | 435/168 |
| 2001/0018197 A1 | 8/2001 | Wong et al. | 435/68.1 |
| 2001/0029042 A1 | 10/2001 | Fouache et al. | 435/243 |

FOREIGN PATENT DOCUMENTS

| | | |
|---|---|---|
| EP | 0 420 358 A1 | 4/1991 |
| EP | 0 449 376 A2 | 10/1991 |
| EP | 0 556 883 A1 | 8/1993 |
| EP | 0 649 600 A1 | 4/1995 |
| EP | 0 684 313 A2 | 11/1995 |
| EP | 0 699 762 A2 | 3/1996 |

(List continued on next page.)

OTHER PUBLICATIONS

PIR–68 Database, Accession No. B36733, corresponding to Greiner et al., Arch. Biochem. Biophys., 303, 107–113, 1993 (cited in the IDS), see the attachment alignment.*
Granovskii et al., "Expression of Hepatitis B Virus HBsAg Gene in Yeast Cells Under Control of Promoter Region of PHO5 Gene," *Soviet Progress in Virology* 5:45–47 (1985).
Touati et al., "Pleiotropic Mutations in appR Reduce pH 2.5 Acid Phosphatase Expression and Restore Succinate Utilisation in CRP–deficient Strains of *Escherichia coli*," *Mol. Gen. Genet.* 202:257–264 (1986).

(List continued on next page.)

*Primary Examiner*—Maryam Monshipouri
(74) *Attorney, Agent, or Firm*—Nixon Peabody LLP

(57) ABSTRACT

The present invention provides phosphatases with improved phytase activity. The invention provides proteolytic fragments of phosphatase having improved phytase activity. A recombinant gene encoding a phosphatase fragment having improved phytase activity is also provided. The invention also includes a method of increasing the phytase activity of phosphatase by treating the phosphatase with a protease. In addition, the invention provides a new phosphatase, AppA2, having improved properties.

6 Claims, 12 Drawing Sheets

FOREIGN PATENT DOCUMENTS

| | | |
|---|---|---|
| EP | 0 772 978 B1 | 5/1997 |
| EP | 0 779 037 A1 | 6/1997 |
| EP | 0 897 010 A2 | 2/1999 |
| EP | 0 897 985 A2 | 2/1999 |
| EP | 0 909 821 A2 | 4/1999 |
| EP | 0 925 723 A1 | 6/1999 |
| EP | 0 955 362 A1 | 11/1999 |
| EP | 0 960 934 A1 | 12/1999 |
| GB | 2 286 396 A | 8/1995 |
| GB | 2 316 082 A | 2/1998 |
| WO | WO 90/05182 | 5/1990 |
| WO | WO 91/05053 | 4/1991 |
| WO | WO 91/14773 | 10/1991 |
| WO | WO 91/14782 | 10/1991 |
| WO | WO 93/14645 | 8/1993 |
| WO | WO 93/16175 | 8/1993 |
| WO | WO 93/19759 | 10/1993 |
| WO | WO 94/03072 | 2/1994 |
| WO | WO 94/03612 | 2/1994 |
| WO | WO 97/16076 | 5/1997 |
| WO | WO 97/35017 | 9/1997 |
| WO | WO 97/39638 | 10/1997 |
| WO | WO 97/45009 | 12/1997 |
| WO | WO 97/48812 | 12/1997 |
| WO | WO 98/05785 | 2/1998 |
| WO | WO 98/06856 | 2/1998 |
| WO | WO 98/20139 | 5/1998 |
| WO | WO 98/30681 | 7/1998 |
| WO | WO 98/44125 | 10/1998 |
| WO | WO 98/54980 | 12/1998 |
| WO | WO 99/08539 | 2/1999 |
| WO | WO 99/49740 | 10/1999 |
| WO | WO 00/10404 | 3/2000 |
| WO | WO 00/20569 | 4/2000 |
| WO | WO 00/41509 A3 | 7/2000 |
| WO | WO 00/47060 | 8/2000 |
| WO | WO 00/71728 A1 | 11/2000 |
| WO | WO 00/72700 A1 | 12/2000 |
| WO | WO 01/58275 A2 | 8/2001 |
| WO | WO 01/58276 A2 | 8/2001 |

OTHER PUBLICATIONS

Sidhu et al., "Analysis of α–Factor Secretion Signals by Fusing with Acid Phosphatase of Yeast," *Gene* 54:175–184 (1987).

Zvonok et al., "Construction of Versatile *Escherichia coli*–Yeast Shuttle Vectors for Promoter Testing in *Saccharomyces cerevisia*," *Gene* 66(2):313–318 (1988).

Dassa et al., "The Complete Nucleotide Sequence of the *Escherichia coli* Gene appA Reveals Significant Homology Between pH 2.5 Acid Phosphatase and Glucose–1–Phosphatase," *Journal of Bacteriology*, 172(9):5497–5500 (1990).

Ostanin et al., "Overexpression, Site–Directed Mutagenesis, and Mechanism of *Escherichia coli* Acid Phosphatase," *Journal of Biological Chemistry* 267(32):22830–22836 (1992).

Ostanin et al., "Asp$^{304}$ of *Escherichia coli* Acid Phosphatase is Involved in Leaving Group Protonation," *J. of Biol. Chem.* 268(28):20778–20784 (1993).

Blondeau et al., "Development of High–Cell–Density Fermentation for Heterologous Interleukin 1β Production in *Kluyveromyces lactis*, Controlled by the PHO5 Promoter," *Appl. Microbiol Biotechnol.* 41:324–329 (1994).

Moore et al., "Molecular Cloning, Expression and Evaluation of Phosphohydrolases for Phytate–Degrading Activity," *Journal of Industrial Microbiology* 14:396–402 (1995).

Verwoerd et al., "Stable Accumulation of *Aspergillus niger* Phytase in Transgenic Tobacco Leaves," *Plant Physiol.* 109:1199–1205 (1995).

Brøndsted et al., "Effect of Growth Conditions on Expression of the Acid Phosphatase (cyx–appA) Operon and the appY Gene, Which Encodes a Transcriptional Activator of *Escherichia coli*," *Journal of Bacteriology* 178(6):1556–1564 (1996).

Murray et al., "Construction of Artificial Chromosomes in Yeast," *Nature* 305:189–193 (1983).

Greiner et al., "Purification and Characterization of Two Phytases from *Escherichia coli*," *Archives of Biochemistry and Biophysics* 303:107–113 (1993).

Minamiguchi et al., "Secretive Expression of the *Aspergillus aculeatus* Cellulase (FI–CM Case) by *Saccharomyces cerevisiae*," *Journal of Fermentation and Bioengineering* 79(4):363–366 (1995).

Wodzinski et al., "Phytase," *Advances in Applied Microbiology* 42:263–302 (1996).

Konietzny et al., "Model Systems for Developing Detection Methods for Foods Deriving from Genetic Engineering," *Journal of Food Composition and Analysis* 10:28–35 (1997).

Sun et al., "Expression of *Aspergillus niger* Phytase in Yeast *Saccharomyces cerevisiae* for Poultry Diet Supplementation," *Poultry Science* 76(Suppl. 1):5 (1997) (abstract only).

Yao et al., "Recombinant *Pichia pastoris* Overexpressing Bioactive Phytase," *Science in China (Series C) Life Sciences* 41(3):330–336 (1998).

Han et al., "Expression of an *Aspergillus niger* Phytase Gene (phyA) in *Saccharomyces cerevisiae*," *Applied and Environmental Microbiology* 65(5):1915–1918 (1999).

Maugenest et al., "Cloning and Characterization of cDNA Encoding a Maize Seedling Phytase," *Biochem. J.* 322:511–517 (1997).

Tschopp et al., "Heterologous Gene Expression in Methylotrophic Yeast," *Biotechnology*, 18:305–322 (1991).

Kumagae et al., "Conversion of Starch to Ethanol in a Recombinant *Saccharomyces cerevisiae* Strain Expressing Rice α–amylase from a Novel *Pichia pastoris* Alcohol Oxidase Promoter," *Biotechnology* 11:606–610 (1993).

Van Hartingsveldt et al., "Cloning, Characterization and Overexpression of the Phytase–Encoding Gene (phyA) of *Aspergillus niger*," *Gene* 127:87–94 (1993).

Phillippy et al., "Expression of an *Aspergillus niger* Phytase (phyA) in *Escherichia coli*," *J. Agric Food Chem.* 45(8):3337–3342 (1997).

Rodriquez et al., "Site–Directed Mutagenesis Improves Catalytic Efficiency and Thermostability of *Escherichia coli* pH 2.5 Acid Phosphatase/Phytase Expressed in *Pichia pastoris*," *Archives of Biochemistry and Biophysics* 382(1):105–112 (2000).

Boer et al., "Characterization of *Trichoderma reesei* Cellobiohydrolase Cel7a Secreted from *Pichia pastoris* Using Two Different Promoters," *Biotechnology and Bioengineering* 69(5):486–494 (2000).

Takahashi et al., "Independent Production of Two Moleclar Forms of a Recombinant *Rhizopus oryae* Lipase by KEX2–Engineered Strains of *Saccharomyces cerevisiae*," *Applied Microbiol. Biotechnology*, 52(4):534–540 (1999).

Meldgaard et al., "Different Effects of N–Glycosylation on the Thermostability of Highly Homologous Bacterial (1,3–1,4)–β–Glucanases Secreted from Yeast," *Microbiology* 140(1):159–166 (1994).

Kanai et al., "Recombinant Thermostable Cycloinulo–oligosaccharide Fructanotransferase Produced by *Saccharomyces cerevisiae*," *Appl. Environ. Microbiol.* 63(12):4956–4960 (1997).

Terashima et al., "The Roles of the N–Linked Carbohydrate Chain of Rice α–amylase in Thermostability and Enzyme Kinetics," *Eur. J. Biochem.* 226:249–254 (1994).

Atlung et al., "Role of the Transcriptional Activator AppY in Regulation of the cyx appA Operon of *Escherichia coli* by Anaerobiosis, Phosphate Starvation, and Growth Phase," *Journal of Bacteriology* 176(17):5414–5422 (1994).

Belin et al., "A Pleiotropic Acid Phosphatase–Deficient Mutant of *Excherichia coli* Shows Premature Termination in the dsbA Gene. Use of dsbA::phoA Fusions to Localize a Structurally Important Domain in DsbA," *Mol. Gen. Genet.* 242:23–32 (1994).

Dassa et al., "Indentification of the Gene appA for the Acid Phosphatase (pH Optimum 2.5) of *Escherichia coli*," *Mol. Gen. Genet.*, 200:68–73 (1985).

Piddington et al., "The Cloning and Sequencing of the Genes Encoding Phytase (phy) and pH 2.5–Optimum Acid Phosphatase (aph) from *Aspergillus niger* var. *awamori*," *Gene*, 133:55–62 (1993).

Jia et al, "Purification, Crystallization and Preliminary X–ray Analysis of the *Escherichia coli* Phytase," *Acta Cryst.*, D54:647–649 (1998).

Kim et al., "Cloning of the Thermostable Phytase Gene (phy) from Bacillus sp. DS11 and its Overexpression in *Escherichia coli*," *FEMS Microbiology Letters*, 162:185–191 (1998).

Kerovuo et al., "Isolation, Characterization, Molecular Gene Cloning, and Sequencing of a Novel Phytase from *Bacillus subtilis*," *Applied and Environmental Microbiology*, 64(6):2079–2085 (1998).

Wyss et al., "Biophysical Characterization of Fungal Phytases (myo–Inositol Hexakisphosphate Phosphohydrolases): Molecular Size, Glycosylation Pattern, and Engineering of Proteolytic Resistance," *Applied and Environment Microbiology*, 65(2):359–366 (1999).

Wyss et al., "Biochemical Characterization of Fungal Phytases (myo–Inositol Hexakisphosphate Phosphohydrolases): Catalytic Properties," *Applied and Environmental Microbiology*, 65(2):367–373 (1999).

Han et al., "Role of Glycosylation in the Functional Expression of an *Aspergillus niger* Phytase (phyA) in *Pichia pastoris*," *Archives of Biochemistry and Biophysics* 364(1):83–90 (1999).

Rodriguez et al., "Different Sensitivity of Recombinant *Aspergillus niger* Phytase (r–PhyA) and *Escherichia coli* pH 2.5 Acid Phosphatase (r–AppA) to Trypsin and Pepsin in Vitro," *Archives of Biochemistry and Biophysics* 365(2):262–267 (1999).

Rodriquez et al., "Cloning, Sequencing, and Expression of an *Escherichia coli* Acid Phosphatase/Phytase Gene (appA2) Isolated from Pig Colon," *Biochemical and Biophysical Research Communications* 257:117–123 (1990).

Divakaran et al., "In Vitro Studies on the Interaction of Phytase with Trypsin and Amylase Extracted from Shrimp (*Penaeus vannamei*) Hepatopancreas," *J. Agric. Food Chem.* 46:4973–4976 (1998).

Dassa et al., "The Complete Nucleotide Sequence of the *Excherichia coli* Gene appA Reveals Significant Homology between pH 2.5 Acid Phosphatase and Glucose–1–Phosphatase," *Journal of Bacteriology* 172(9):5497–5500 (1990).

* cited by examiner

```
  1 taaggaqcaqaaaca ATG TGG TAT TTC CTT TGG TTC GTC GGC ATT TTG TTG ATG TGT TCG CTC   63
  1                 M   W   Y   F   L   W   F   V   G   I   L   L   M   C   S   L    16

64 TCC ACC CTT GTG TTG GTA TGG CTG GAC CCG CGA TTG AAA AGT TAAcgaacgtaagcctgatccgg  128
 17 S   T   L   V   L   V   W   L   D   P   R   L   K   S   *                         31

129 cgcattagcgtcgatcaggcaataatatcggatatcaaagcggaaacatatcg ATG AAA GCG ATC TTA ATC    201
  1                                                       M   K   A   I   L   I        6

←——————— E2 ———————→
202 CCA TTT TTA TCT CTT TTG ATT CCG TTA ACC CCG CAA TCT GCA TTC GCT CAG AGT GAG CCG  261
  7 P   F   L   S   L   L   I   P   L   T   P   Q   S   A   F   A   Q   S   E   P     26

262 GAG CTG AAG CTG GAA AGT GTG GTG ATT GTC AGC CGT CAT GGT GTG CGT GCC CCA ACC AAG  321
 27 E   L   K   L   E   S   V   V   I   V   S   R   H   G   V   R   A   P   T   K     46

322 GCC ACG CAA CTG ATG CAG GAT GTC ACC CCA GAC GCA TGG CCA ACC TGG CCG GTA AAA CTG  381
 47 A   T   Q   L   M   Q   D   V   T   P   D   A   W   P   T   W   P   V   K   L     66

382 GGT TGG CTG ACA CCA CGC GGT GGT GAG CTA ATC GCC TAT CTC GGA CAT TAC CAA CGC CAG  441
 67 G   W   L   T   P   R   G   G   E   L   I   A   Y   L   G   H   Y   Q   R   Q     86

442 CGT CTG GTG GCC GAC GGA TTG CTG GCG AAA AAG GGC TGC CCG CAG CCT GGT CAG GTC GCG  501
 87 R   L   V   A   D   G   L   L   A   K   K   G   C   P   Q   P   G   Q   V   A    106

502 ATT ATT GCT GAT GTC GAC GAG CGT ACC CGT AAA ACA GGC GAA GCC TTC GCC GCC GGG CTG  561
107 I   I   A   D   V   D   E   R   T   R   K   T   G   E   A   F   A   A   G   L    126

562 GCA CCT GAC TGT GCA ATA ACC GTA CAT ACC CAG GCA GAT ACG TCC AGT CCC GAT CCG TTA  621
127 A   P   D   C   A   I   T   V   H   T   Q   A   D   T   S   S   P   D   P   L    146

622 TTT AAT CCT CTA AAA ACT GGC GTT TGC CAA CTG GAT AAC GCG AAC GTG ACT GAC GCG ATC  681
147 F   N   P   L   K   T   G   V   C   Q   L   D   N   A   N   V   T   D   A   I    166

682 CTC AGC AGG GCA GGA GGG TCA ATT GCT GAC TTT ACC GGG CAT CGG CAA ACG GCG TTT CGC  741
167 L   S   R   A   G   G   S   I   A   D   F   T   G   H   R   Q   T   A   F   R    186

742 GAA CTG GAA CGG GTG CTT AAT TTT TCC CAA TTA AAC TTG TGC CTT AAC CGT GAG AAA CAG  801
187 E   L   E   R   V   L   N   F   S   Q   L   N   L   C   L   N   R   E   K   Q    206

802 GAC GAA AGC TGT TCA TTA ACG CAG GCA TTA CCA TCG GAA CTC AAG GTG AGC GCC GAC AAT  861
207 D   E   S   C   S   L   T   Q   A   L   P   S   E   L   K   V   S   A   D   N    226

862 GTT TCA TTA ACC GGT GCG GTA AGC CTC GCA TCA ATG CTG ACG GAA ATA TTT CTC CTG CAA  921
227 V   S   L   T   G   A   V   S   L   A   S   M   L   T   E   I   F   L   L   Q    246

922 CAA GCA CAG GGA ATG CCG GAG CCG GGG TGG GGA AGG ATC ACT GAT TCA CAC CAG TGG AAC  981
247 Q   A   Q   G   M   P   E   P   G   W   G   R   I   T   D   S   H   Q   W   N    266

982 ACC TTG CTA AGT TTG CAT AAC GCG CAA TTT TAT TTA CTA CAA CGC ACG CCA GAG GTT GCC 1041
 267 T   L   L   S   L   H   N   A   Q   F   Y   L   L   Q   R   T   P   E   V   A    286

1042 CGC AGT CGC GCC ACC CCG TTA TTG GAT TTG ATC ATG GCA GCG TTG ACG CCC CAT CCA CCG 1101
 287 R   S   R   A   T   P   L   L   D   L   I   M   A   A   L   T   P   H   P   P    306

1102 CAA AAA CAG GCG TAT GGT GTG ACA TTA CCC ACT TCA GTG CTG TTT ATT GCC GGA CAC GAT 1161
 307 Q   K   Q   A   Y   G   V   T   L   P   T   S   V   L   F   I   A   G   H   D    326

1162 ACT AAT CTG GCA AAT CTC GGC GGC GCA CTG GAG CTC AAC TGG ACG CTT CCA GGT CAG CCG 1221
 327 T   N   L   A   N   L   G   G   A   L   E   L   N   W   T   L   P   G   Q   P    346

1222 GAT AAC ACG CCG CCA GGT GGT GAA CTG GTG TTT GAA CGC TGG CGT CGG CTA AGC GAT AAC 1281
 347 D   N   T   P   P   G   G   E   L   V   F   E   R   W   R   R   L   S   D   N    366

1282 AGC CAG TGG ATT CAG GTT TCG CTG GTC TTC CAG ACT TTA CAG CAG ATG CGT GAT AAA ACG 1341
 367 S   Q   W   I   Q   V   S   L   V   F   Q   T   L   Q   Q   M   R   D   K   T    386

1342 CCG CTA TCA TTA AAT ACG CCG CCC GGA GAG GTG AAA CTG ACC CTG GCA GGA TGT GAA GAG 1401
 387 P   L   S   L   N   T   P   P   G   E   V   K   L   T   L   A   G   C   E   E    406

1402 CGA AAT GCG CAG GGC ATG TGT TCG TTG GCC GGT TTT ACG CAA ATC GTG AAT GAA GCG CGC 1461
 407 R   N   A   Q   G   M   C   S   L   A   G   F   T   Q   I   V   N   E   A   R    426

←——————— K2 ———————
1462 ATA CCG GCG TGC AGT TTG TAA TGGTACCCC                                            1491
 427 I   P   A   C   S   L   *                                                         433
```

ENZYMES WITH IMPROVED PHYTASE ACTIVITY

The present application claims the benefit of U.S. Provisional Patent Application Ser. No. 60/127,032, filed Mar. 31, 1999.

BACKGROUND OF THE INVENTION

Phytases are myo-inositol hexakisphosphate phosphohydrolases that catalyze the stepwise removal of inorganic orthophosphate from phytate (myo-inositol hexakisphosphate) (1). There are two types of phytases. One is called 3-phytase (EC.3.1.3.8) which initiates the removal of phosphate groups at the positions 1 and 3 of the myo-inositol ring. The other is called 6-phytase (EC.3.1.3.26) which first frees the phosphate at the position 6 of the ring. While no phytase has been identified from animal tissues, plants usually contain 6-phytases and a broad range of microorganisms, including bacteria, filamentous fungi, and yeast, produce 3-phytases (2–9). Because over 70% of the total phosphorus in foods or feeds of plant origin is in the form of phytate that is poorly available to simple-stomached animals and humans, phytases are of great uses in improving mineral nutrition of these species (10–16). Supplemental microbial phytases in diets for swine and poultry effectively enhance bioavailability of phytate phosphorus and reduce the need for inorganic phosphorus supplementation (11–15), resulting less phosphorus pollution in areas of intensive animal production (8–15). However, a relatively high level of phytase supplementation is necessary in animal diets (10–16), because a considerable amount of the enzyme is degraded in stomach and small intestine (13), probably by proteolysis of pepsin and trypsin. Meanwhile, the proteolytic profiles of various phytases were not studied. Clearly, a better understanding of their sensitivities to trypsin and pepsin hydrolysis could be helpful for improving the nutritional value of phytases. *Aspergillus niger* phytase gene (phyA) has been overexpressed in its original host (17) and the recombinant enzyme (r-PhyA, EC 3.1.3.8) has been used in animal diets as a commercial phytase (13, 14). This enzyme is a glycoprotein of approximately 80 kDa. *Escherichia coli* pH 2.5 acid phosphatase gene (appA) has also been characterized (18, 19). Animal experiments have demonstrated that the recombinant enzyme (r-AppA, EC: 3.1.3.2) is as effective as r-PhyA in releasing phytate phosphorus in animal diets (14).

But, expenses of the limited available commercial phytase supply and the activity instability of the enzyme to heat of feed pelleting preclude its practical use in animal industry. Therefore, there is a need for enzymes which have a high level of phytase activity and a high level of stability for use in animal feed.

SUMMARY OF THE INVENTION

The present invention provides a phosphatase fragment having improved phytase activity. A fragment of a phosphatase having increased phytase activity is produced by treating the phosphatase with a protease.

The invention further provides a recombinant gene encoding a phosphatase fragment having improved phytase activity. The vector consists of a promoter, a coding region encoding the phosphatase fragment, and a terminator.

In another embodiment, the invention provides a method of increasing the phytase activity of phosphatase by treating the phosphatase with a protease.

The invention also provides a phosphatase having improved phytase activity, which has an amino acid sequence as shown in SEQ. ID No. 1.

BRIEF DESCRIPTION OF THE DRAWINGS

FIG. 1 shows the change in phytase activity after protease digestion.

FIG. 6 shows the nucleotide sequence of the appA2 gene and its deduced amino acid sequence. The untranslated region is indicated by lowercase letters. The underlined sequences are the primers used to amplify appA2'(Pf1: 1–22, and K2: 1467–1480), appA2 (E2: 247–26 1, and K2: 1467–1480). Potential N-glycosylation sites are boxed. The sequence of appA2 has been transmitted to Genebank data library with accession number 250016. The appA2' gene is formed by nucleotides 1–1489 (SEQ. ID. No. 9). The deduced amino acid sequence of the appA2 gene is identified as amino acids 1–433 (SEQ. ID. No. 1), corresponding to nucleic acid bases 182–1480 of the appA2' gene. A lead amino acid sequence encoded by the appA2 gene is identified as amino acids 1–30 (i.e., SEQ. ID. No. 8) of the first numbered amino acid sequence, and corresponds to nucleic acid bases 16–105 of SEQ. ID. No. 9.

DETAILED DESCRIPTION OF THE INVENTION

Figure 1A:
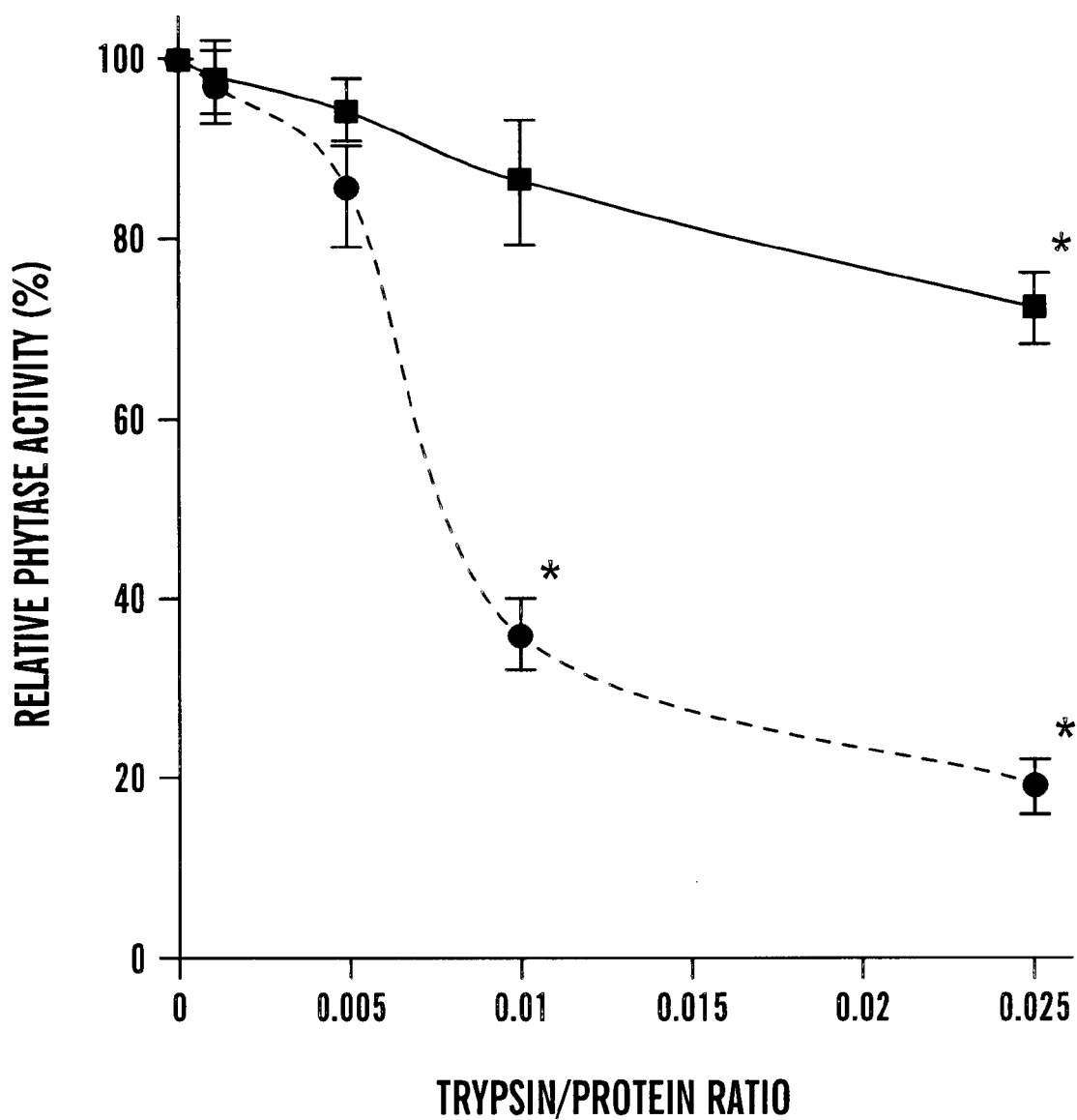
FIG. 1A shows phytase activity changes of r-PhyA and r-AppA incubated with different ratios of trypsin/protein (w/w) (r=0.001, 0.005, 0.01, and 0.025). Symbols: r-PhyA (■) and r-AppA (●). The results are the mean±SEM from five independent experiments. * indicates statistical significance (P<0.01) versus untreated r-PhyA or r-AppA control.

The present invention provides phosphatases having improved phytase activity.

One embodiment of the invention provides a phosphatase fragment having improved phytase activity. The phosphatase is treated with a protease and fragments having phosphatase activity are selected. As discussed in further detail below, these fragments, have improved phytase activity compared to the full length peptide.

In a preferred embodiment, the protease is pepsin.

In addition to producing the active fragment by proteolysis of the full length peptide, the present invention also provides a recombinant gene having a promoter, a coding region encoding the phosphatase fragment according to claim 1, and a terminator. The recombinant gene can be used to express the truncated product directly.

The improved phosphatases can by used in animal feed to improve the accessibility of phosphate to the animal.

In addition to the phosphatase, the invention provides a method of increasing the phytase activity of phosphatase by treating the phosphatase with a protease.

In another embodiment, the invention provides a phosphatase having improved phytase activity, which has an amino acid sequence as shown in SEQ. ID No. 1 as shown in FIG. 6.

Preferably, the protein or polypeptide with phytase activity is secreted by the cell into growth media. This allows for higher expression levels and easier isolation of the product. The protein or polypeptide with phytase activity is coupled to a signal sequence capable of directing the protein out of the cell. Preferably, the signal sequence is cleaved from the protein.

In a preferred embodiment, the heterologous gene, which encodes a protein or polypeptide with phytase activity, is spliced in frame with a transcriptional enhancer element.

A preferred phosphatase is encoded by the appA gene of *E. coli*. The gene, originally defined as *E. coli* periplasmic phosphoanhydride phosphohydrolase (appA) gene, contains 1,298 nucleotides (GeneBank accession number: M58708). The gene was first found to code for an acid phosphatase protein of optimal pH of 2.5 (EcAP) in *E. coli*. The acid phosphatase is a monomer with a molecular mass of 44,644 daltons. Mature EcAP contains 410 amino acids (18). Ostanin, et al. overexpressed appA in *E. coli* BL21 using a pT7 vector and increased its acid phosphatase activity by approximately 400-folds (440 mU/mg protein) (20). The product of the appA gene was not previously known to have phytase activity.

The phosphatase can be expressed in any prokaryotic or eukaryotic expression system. A variety of host-vector systems may be utilized to express the protein-encoding sequence(s). Preferred vectors include a viral vector, plasmid, cosmid or an oligonucleotide. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Preferred hosts for expressing phosphatase include fungal cells, including species of yeast or filamentous fungi, may be used as host cells in accordance with the present invention. Preferred yeast host cells include different strains of *Saccharomyces cerevisiae*. Other yeasts like Kluyveromyces, Torulaspora, and Schizosaccharomyces can also be used. In a preferred embodiment, the yeast strain used to overexpress the protein is *Saccharomyces cerevisiae*. Filamentous fungi host cells include Aspergillus and Neurospora.

In another embodiment of the present invention, the yeast strain is a methylotrophic yeast strain. Methylotrophic yeast are those yeast genera capable of utilizing methanol as a carbon source for the production of the energy resources necessary to maintain cellular function and containing a gene for the expression of alcohol oxidase. Typical methylotrophic yeasts include members of the genera Pichia, Hansenula, Torulopsis, Candida, and Karwinskia. These yeast genera can use methanol as a sole carbon source. In a preferred embodiment, the methylotrophic yeast strain is *Pichia pastoris*.

A preferred embodiment of the invention is a protein or polypeptide having phytase activity with optimum activity in a temperature range of 57 to 65° C. A more preferred embodiment is a protein or polypeptide having phytase activity, where its temperature range for optimum activity is from 58 to 62° C.

Yet another preferred embodiment is a protein or polypeptide having phytase activity where the protein retains at least 40% of its activity after heating the protein for 15 minutes at 80° C. More preferred is a protein or polypeptide having phytase activity where the protein retains at least 60% of its activity after heating the protein for 15 minutes at 60° C.

Purified protein may be obtained by several methods. The protein or polypeptide of the present invention is preferably produced in purified form (preferably at least about 80%, more preferably 90%, pure) by conventional techniques. Typically, the protein or polypeptide of the present invention is secreted into the growth medium of recombinant host cells. Alternatively, the protein or polypeptide of the present invention is produced but not secreted into growth medium. In such cases, to isolate the protein, the host cell carrying a recombinant plasmid is propagated, lysed by sonication, heat, or chemical treatment, and the homogenate is centrifuged to remove cell debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

The present invention also provides a yeast strain having a heterologous gene which encodes a protein or polypeptide with phytase activity. The heterologous gene should be functionally linked to a promoter capable of expressing phytase in yeast and followed by a transcriptional terminator.

Yet another aspect of the invention is a vector for expressing phytase in a host. The vector carries a phosphatase gene which encodes a protein or polypeptide with phytase activity.

For cloning into yeast, the gene can be cloned into any vector which replicates autonomously or integrates into the genome of yeast. The copy number of autonomously replicating plasmids, e.g. YEp plasmids may be high, but their mitotic stability may be insufficient (48). They may contain the 2 mu-plasmid sequence responsible for autonomous replication, and an E. coli sequence responsible for replication in E. coli. The vectors preferably contain a genetic marker for selection of yeast transformants, and an antibiotic resistance gene for selection in E. coli. The episomal vectors containing the ARS and CEN sequences occur as a single copy per cell, and they are more stable than the YEp vectors. Integrative vectors are used when a DNA fragment is integrated as one or multiple copies into the yeast genome. In this case, the recombinant DNA is stable and no selection is needed (49–51). Some vectors have an origin of replication, which functions in the selected host cell. Suitable origins of replication include $2\mu$, ARS1, and $25\,\mu$M. The vectors have restriction endonuclease sites for insertion of the fusion gene and promoter sequences, and selection markers. The vectors may be modified by removal or addition of restriction sites, or removal of other unwanted nucleotides.

The phytase gene can be placed under the control of any promoter (52). One can choose a constitutive or regulated yeast promoter. Suitable promoter sequences for yeast vectors include, among others, promoters for metallothionein, 3-phosphoglycerate kinase (53) or other glycolytic enzymes (54), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in EP A-73,657 to Hitzeman, which is hereby incorporated by reference. Another alternative is the glucose-repressible ADH2 promoter (56, 57), which are hereby incorporated by reference.

One can choose a constitutive or regulated yeast promoter. The strong promoters of e.g., phosphoglycerate kinase (PGK) gene, other genes encoding glycolytic enzymes, and the alpha -factor gene, are constitutive. When a constitutive promoter is used, the product is synthesized during cell growth. The ADH2 promoter is regulated with ethanol and glucose, the GAL-1-10 and GAL7 promoters with galactose and glucose, the PHO5 promoter with phosphate, and the metallothionine promoter with copper. The heat shock promoters, to which the HSP150 promoter belongs, are regulated by temperature. Hybrid promoters can also be used. A regulated promoter is used when continuous expression of the desired product is harmful for the host cells. Instead of yeast promoters, a strong prokaryotic promoter such as the T7 promoter, can be used, but in this case the yeast strain has to be transformed with a gene encoding the respective polymerase. For transcription termination, the HSP150 terminator, or any other functional terminator is used. Here, promoters and terminators are called control elements. The present invention is not restricted to any specific vector, promoter, or terminator.

The vector may also carry a selectable marker. Selectable markers are often antibiotic resistance genes or genes capable of complementing strains of yeast having well characterized metabolic deficiencies, such as tryptophan or histidine deficient mutants. Preferred selectable markers include URA3, LEU2, HIS3, TRP1, HIS4, ARG4, or antibiotic resistance genes.

The vector may also have an origin of replication capable of replication in a bacterial cell. Manipulation of vectors is more efficient in bacterial strains. Preferred bacterial origin of replications are ColE1, Ori, or oriT.

A leader sequence either from the yeast or from phytase genes or other sources can be used to support the secretion of expressed phytase enzyme into the medium. The present invention is not restricted to any specific type of leader sequence or signal peptide.

Suitable leader sequences include the yeast alpha factor leader sequence, which may be employed to direct secretion of the phytase. The alpha factor leader sequence is often inserted between the promoter sequence and the structural gene sequence (58; U.S. Pat. No. 4,546,082; and European published patent application No. 324,274, which are hereby incorporated by reference). Another suitable leader sequence is the S. cerevisiae MF alpha 1 (alpha-factor) is synthesized as a prepro form of 165 amino acids comprising signal-or prepeptide of 19 amino acids followed by a "leader" or propeptide of 64 amino acids, encompassing three N-linked glycosylation sites followed by (LysArg(Asp/Glu, Ala)2–3 alpha-factor)4 (58). The signal-leader part of the preproMF alpha 1 has been widely employed to obtain synthesis and secretion of heterologous proteins in S. cerivisiae. Use of signal/leader peptides homologous to yeast is known from. U.S. Pat. No. 4,546,082, European Patent Applications Nos. 116,201; 123,294; 123,544; 163,529; and 123,289 and DK Patent Application No. 3614/83, which are hereby incorporated by reference. In European Patent Application No. 123,289, which is hereby incorporated by reference, utilization of the S. cerevisiae a-factor precursor is described whereas WO 84/01153, which is hereby incorporated by reference, indicates utilization of the Saccharomyces cerevisiae invertase signal peptide, and German Patent Application DK 3614/83, which is hereby incorporated by reference, indicates utilization of the Sacchalomyces cerevisiae PH05 signal peptide for secretion of foreign proteins.

The alpha -factor signal-leader from Saccharomyces cerevisiae (MF alpha 1 or MF alpha 2) may also be utilized in the secretion process of expressed heterologous proteins in yeast (U.S. Pat. No. 4,546,082, European Patent Applications Nos. 16,201; 123,294; 123 544; and 163,529, which are hereby incorporated by reference). By fusing a DNA sequence encoding the *S. cerevisiea* MF alpha 1 signal/ leader sequence at the 5' end of the gene for the desired protein secretion and processing of the desired protein was demonstrated. The use of the mouse salivary amylase signal peptide (or a mutant thereof) to provide secretion of heterologous proteins expressed in yeast has been described in Published PCT Applications Nos. WO 89/02463 and WO 90/10075, which are hereby incorporated by reference.

U.S. Pat. No. 5,726,038 describes the use of the signal peptide of the yeast aspartic protease 3, which is capable of providing improved secretion of proteins expressed in yeast. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described in Hinnen et al. (59). The Hinnen et al. protocol selects for Trp transformants in a selective medium, wherein the selective medium consists of 0.67% yeast nitrogen base, 0.5% casamino acids, 2% glucose, 10 μg/ml adenine and 20 μg/ml uracil.

The gene may be maintained on stable expression vector, an artificial chromosome, or by integration into the yeast host cell chromosome. Integration into the chromosome may be accomplished by cloning the phytase gene into a vector which will recombine into a yeast chromosome. Suitable vectors may include nucleotide sequences which are homologous to nucleotide sequences in the yeast chromosome. Alternatively, the phytase gene may be located between recombination sites, such as transposable elements, which can mobilize the gene into the chromosome.

The present invention also provides a method of producing phytase by providing an isolated phosphatase gene, which encodes a protein or polypeptide with phytase activity, and expressing the gene in host cell. The phosphatase preferably is a microbial phosphatase. In a more preferred embodiment, the microbial phosphatase is an *Escherichia coli* phosphatase. Also preferred are the microbial phosphatases, AppA and AppA2.

A method of converting phytate to inositol and inorganic phosphorus is also provided. An appA gene is isolated from an organism, using techniques well known in the art. A protein or polypeptide with phytase activity is then expressed from the gene in a host cell. The resulting protein or polypeptide is mixed or contacted with phytate. This technique is especially useful for treating phytate in food or animal feed.

The preferred appA gene is isolated from *Escherichia coli*.

While the phytase enzyme produced in a yeast system released phytate-P from corn and soy as effectively as the currently commercial phytase, it appeared to be more thermostable. This phytase overexpression system in yeast can be used to provide thermostable phytase for use in the food and feed industries.

EXAMPLES

Example 1

Materials and Methods for Examples 2–6

Expression of r-AppA. The appA gene (Genebank accession number M58708) was obtained from *E. coli* BL21 strain transformed by an expression vector pAPPA1 (20). A 1.35 kb DNA fragment containing the coding region of appA was amplified by PCR following the manufacturer instructions (Perkin Elmer). Primers were derived from 5' and 3' regions of the nucleotide sequence (18), and include: E2 [forward: 242–252]:

5'GGAATTCCAGAGTGAGCCGGA3' (SEQ. ID. No. 2) and K2 [reverse: 1468–1490]: 5'GGGGTACCTTA-CAAACTGCACG3' (SEQ. ID. No. 3). These two primers were synthesized by the Cornell University Oligonucleotide Synthesis Facility (Ithaca, N.Y.). The amplified product was sliced from a 1% agarose gel, and eluted with GENECLEAN II kit (Bio101). The purified fragment was first cloned into pGEM T-easy vector (Promega), and then inserted into the yeast expression vector pPIcZαA (Invitrogen) at EcoRI site. *E. coli* strain TOP10F' (Invitrogen) was used as an initial host to amplify these two constructs. The pPIcZtαA vector containing appA was transformed into *P. pastoris* strain X33 by electroporation according to the manufacturer's instructions (Invitrogen). The transformed cells were plated into YPD-Zeocin agar medium and positive colonies were incubated in minimal media with glycerol (BMGY) for 24 h. When the yeast cell density reached $2.5 \times 10^8$ cells/ml ($OD_{600}$=5), the cells were centrifuged and suspended in 0.5% methanol medium (BMMY) to induce the appA gene expression. Total yeast genomic DNA was extracted from the transformed X33 cells after induction and used as a template to check the presence of the appA gene by PCR using the same primers as described above. The amplified DNA fragment was sequenced at the Cornell University DNA Services-Facility using Taq Cycle automated sequencing with Dye Deoxy terminators (Applied Biosystems, Forster City, Calif.).

Purification of r-PhyA and r-AppA. r-PhyA was obtained from BASF (Mt Olive, N.J.). Both r-PhyA and r-AppA enzymes were initially suspended into 50 mM Tris-HCl, pH 7, and ammonium sulfate was added to 25% of saturation. After the mixture was centrifuged (25,000 g, 20 min), the supernatant was saved and ammonium sulfate was added to 75% of saturation. Then, the mixture was centrifuged (25,000 g, 20 min) and the pellet was suspended into 10 mL of 25 mM Tris-HCl, pH 7. The suspension was dialyzed overnight against the same buffer and loaded onto a DEAE-Sepharose column (Sigma) equilibrated with 25 mM Tris-HCl, pH 7. Proteins were diluted with 0.2 M NaCl, 25 mM Tris-HCl, pH 7 after the column was washed with 200 n-LL of 25 mM Tris-HCl, pH 7. All the collected fractions were assayed for phytase activity and protein concentration (21). The whole purification was conducted at 4° C., and the fractions were stored at −20° C. before analysis.

Proteolysis and protein electrophoresis. The purified r-AppA and r-PhyA (2 mg/mL) were incubated with different amounts of pepsin and trypsin following the manufacturer instructions (Sigma). Pepsin (800 units/mg protein) and trypsin (1,500 BAEE units/mg protein) were dissolved into 10 mM HCl, pH 2 (0.1 mg/mL) and 80 mM ammonium bicarbonate, pH 7.5 (0.1 mg/mL), respectively. One BAEE unit was defined as 0.001 absorbance change at 253 nm per minute at pH 7.6 and 250C, with BAEE as a substrate. In a final volume of 100 μL, 10 μg of purified r-PhyA (0.1 PU) or r-AppA (0.08 PU) was incubated with trypsin or pepsin at protease/phytase (w/w) ratios ranging from 0.001 to 0.01, at 37° C. for 1 to 120 min. The reaction was stopped on ice and the pH of the mixture was adjusted to 8 for protein electrophoresis and phytase activity assay. The digested protein mixtures were analyzed by sodium dodecyl sulfate (SDS)- polyacrylamide or urea-SDS-polyacrylamide gel electrophoresis as previously described (22, 23).

Phytase activity and hydrolysis of phytate phosphorus from soybean meal. Phytase activities of both r-PhyA and r-AppA, prior to or at various time points of proteolysis, were determined as previously described (24). The released inorganic phosphorus (iP) was assayed by the method of Chen et al. (25). One phytase unit (PU) was defined as the activity that releases 1 μmol of iP from sodium phytate per minute at 37° C. To confirm the proteotytic effects of trypsin and pepsin on the residual activities of r-PhyA and r-AppA, the hydrolysis of phytate phosphorus from soybean meal by these two enzymes incubated with different amounts of trypsin or pepsin was monitored. In a 5 mL total reaction, 0.5 mg of the purified r-PhyA (5 PU) or r-AppA (4 PU) was incubated with 1 g soybean meal and pepsin in 10 mM HCl, pH 2.5 or trypsin in 0.2 M citrate, pH 6.8 at 3 VC for 2 h. The released iP was determined as described above.

Example 2

Preparation of r-AppA and r-PhyA

Over 30 colonies of X33 transformed with the appA gene expressed extracellular phytase activity that hydrolyzes sodium phytate. Colony 26 had the highest activity (88 U/mL) and was chosen for further studies. After the r-PhyA and the r-AppA samples were eluted from the DEAE-Sepharose column, 45 fractions of 4 mL each were collected for both enzymes to assay for phytase activity. The fractions used for proteolysis had a specific phytase activity of 9.6 and 8.1 U/mg of protein for the r-PhyA and r-AppA, respectively.

Example 3

Effects of Trypsin Digestion on the Phytase Activities of Both Enzymes

Figure 2:
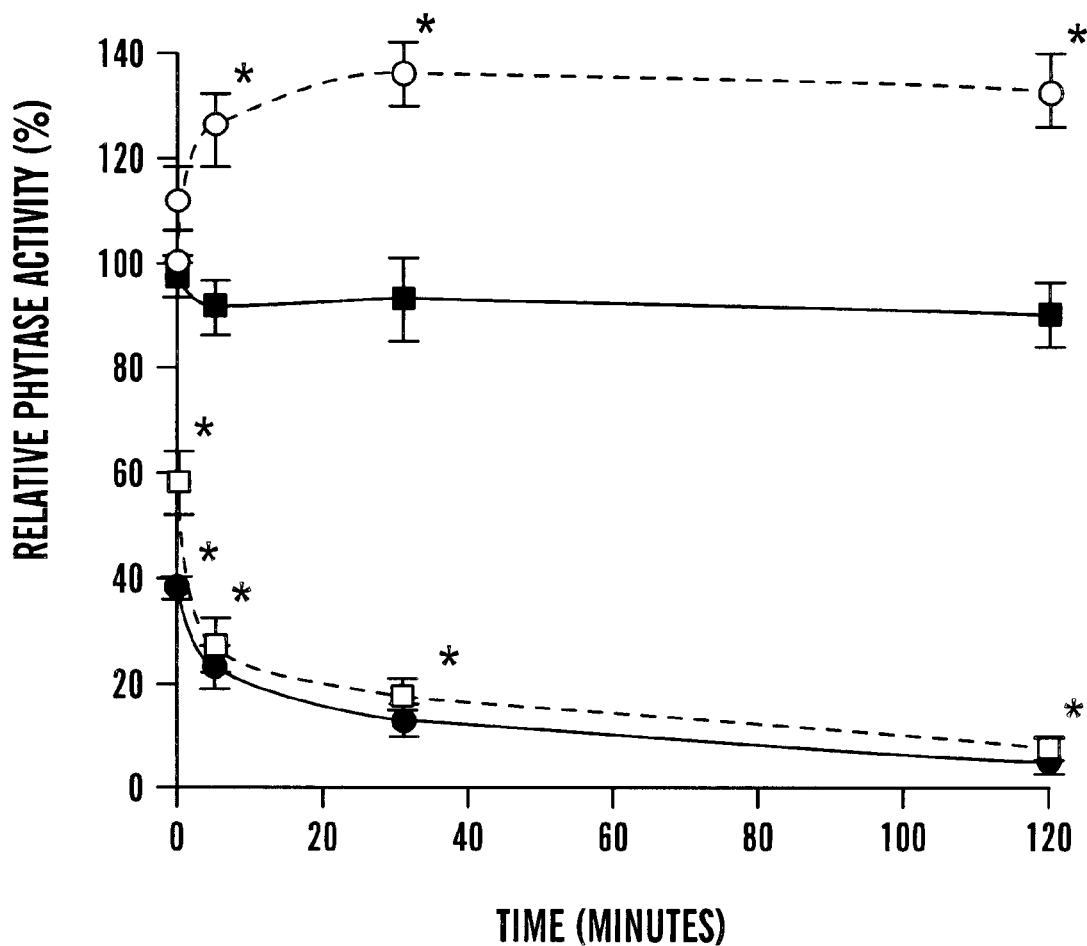
FIG. 2 shows residual phytase activity of r-PhyA and r-AppA after trypsin or pepsin hydrolysis during a time course (0, 1, 51 30, and 120 min). Symbols: trypsin-digested r-PhyA (■) or r-AppA (●); pepsin-digested r-PhyA (□) and r-AppA (○). The ratio of trypsin/phytase (w/w) used was: r=0.01 (w/w). The ratio of pepsin/phytase used was: r=0.005. The results are the mean±SEM from six independent experiments. * indicates statistical significance (P<0.01) versus untreated r-PhyA or r-AppA control.

After 2 hour trypsin digestion, there were significant differences in the residual phytase activities between the r-PhyA and the r-AppA (FIG. 1A). Although both enzymes retained more than 85% of their original activities at the trypsin/phytase ratios of 0.001 and 0.005, r-AppA lost 64 and 74% of its original activity at the ratio of 0.01 and 0.025, respectively. Meanwhile, r-PhyA lost only 14 and 23% of its original activity, respectively. Because of the apparent difference in sensitivities of these two enzymes to trypsin digestion at the ratio of 0.01, a time course study was conducted with this ratio. Up to 2 hour trypsin digestion, r-PhyA still retained 90% of its original activity (FIG. 2). In contrast, r-AppA lost 64, 77, 87, and 95% of its original activity after 1, 5, 30, and 120 minute digestion, respectively.

Example 4

Effect of Pepsin Digestion on the Phytase Activities of Both Enzymes

Figure 1B:
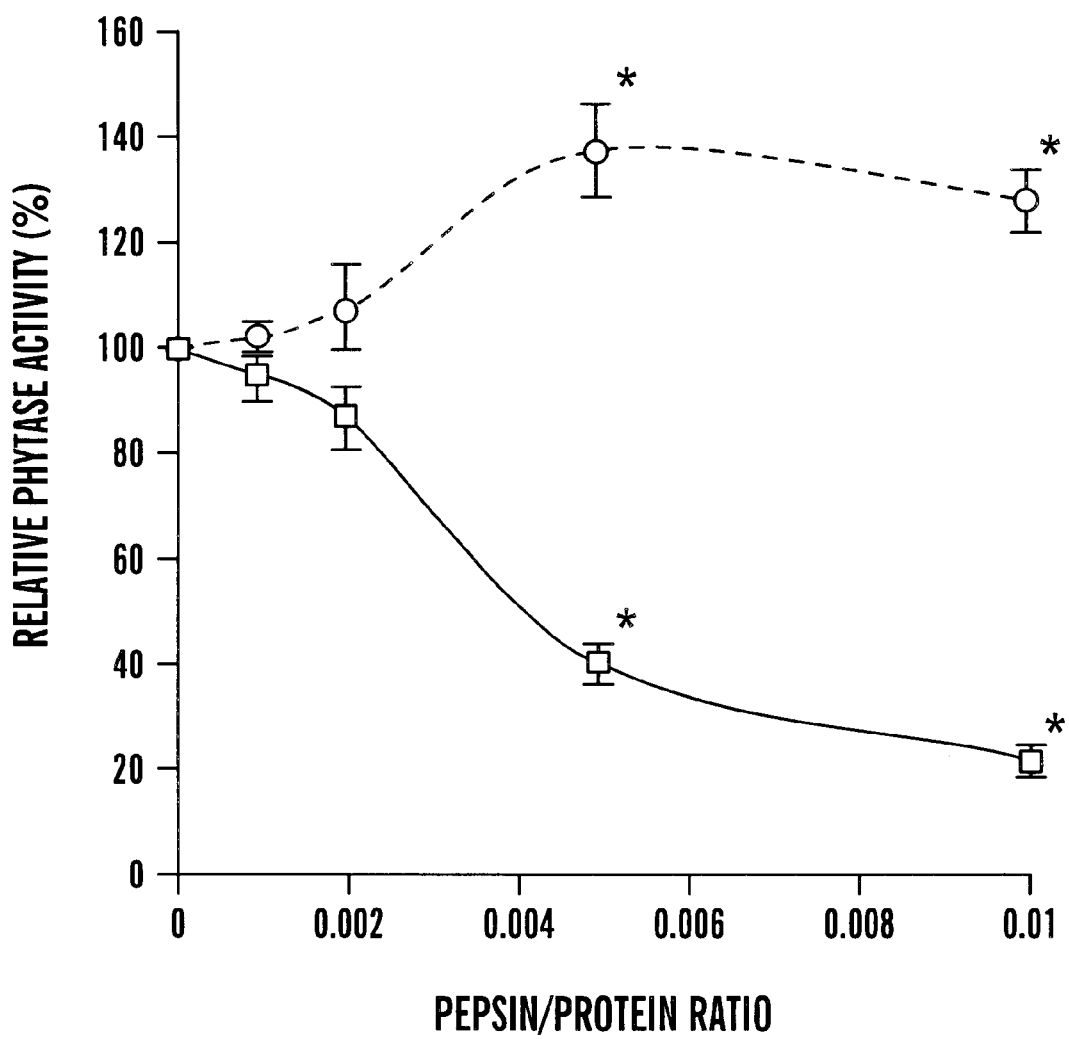
FIG. 1B shows phytase activity changes of r-PhyA and r-AppA incubated with different ratios of pepsin/protein (w/w) (r=0.001, 0.002, 0.005, and 0.01. Symbols: r-PhyA (□) and r-AppA (○). The results are the mean±SEM from seven independent experiments. * indicates statistical significance (P<0.01) versus untreated r-PhyA or r-AppA control.

After 2 hour pepsin digestion, the residual phytase activity of r-AppA was totally unexpected. At the ratios of 0.001 and 0.002, the phytase activity either remained unchanged or slightly increased. At the ratios of 0.005 and 0.01, the phytase activity was enhanced by 30% compared with the initial value. However, r-PhyA lost 58 and 77% of its original activity at these two high ratios (FIG. 1B). Because significantly different responses between r-PhyA and r-AppA at the ratio of 0.005, this ratio was used for a follow-up time course study. There was a stepwise increase in phytase activity along with time when the r-AppA was incubated with pepsin from 0 to 30 min. Thereafter no further increase was observed (FIG. 2). However, r-PhyA lost 42, 73, 82, and 92% of its original activity after 1, 5, 30, and 120 minute incubation, respectively.

Example 5

SDS-polyacrylamide Gel Electrophoresis

Figure 3A:
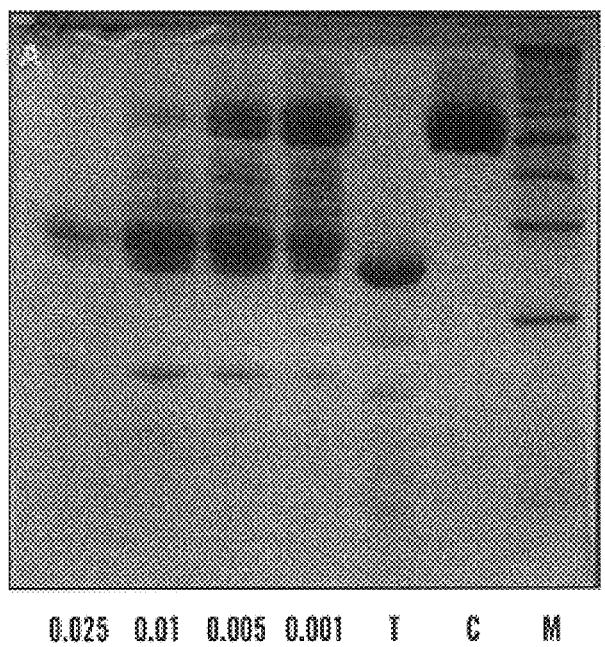
FIG. 3 shows the results of SDS-polyacrylamide gel electrophoresis of r-AppA (12%, Panel A) or r-PhyA (20%, Panel B) digested products by different amounts of trypsin (r=0.001, 0.00 5, 0.01, and 0.025, (w/w). Proteins were stained using Coomasie blue. T: trypsin control, C: purified r-AppA (Panel A) or r-PhyA (Panel B). The protein marker (M) is a 10 kDa ladder [10, 20, 30, 40, 50, 60, 70, 80, 90, 100, 110, 120, and 200 kDa) (Gibco). The results are representative from four independent experiments.
Figure 3B:
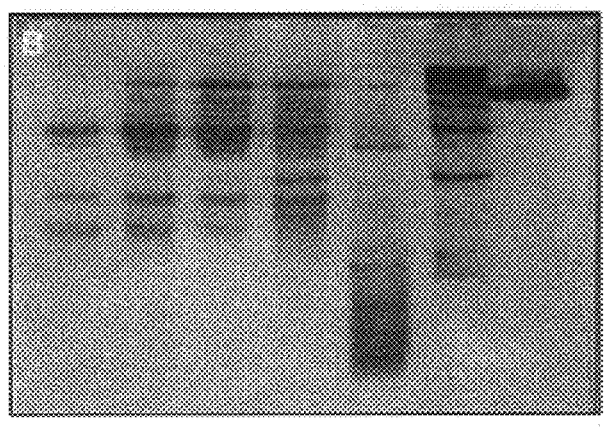
Figure 4A:
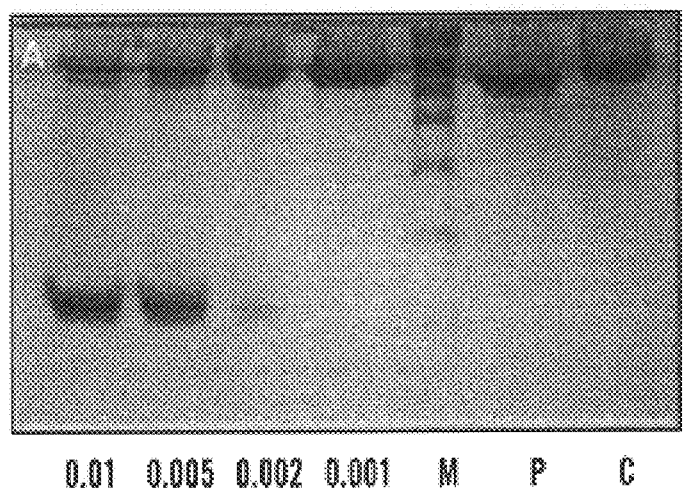
FIG. 4 shows the results from SDS-polyacrylamide gel (20%) electrophoresis of r-AppA (FIG. 4A) or r-PhyA (FIG. 4B) digested products by different amounts of pepsin (r=0.001, 0.002, 0.005, and 0.01, (w/w)). Proteins were stained using Coomasie blue. T: trypsin control, C: purified r-AppA (FIG. 4A) or r-PhyA (FIG. 4B). The protein marker (M) is a 10 kDa ladder [10, 20, 30, 40, 50, 60, 70, 80, 90, 100, 110, 120, and 200 kDa) (Gibco). The results are representative from six independent experiments.
Figure 4B:
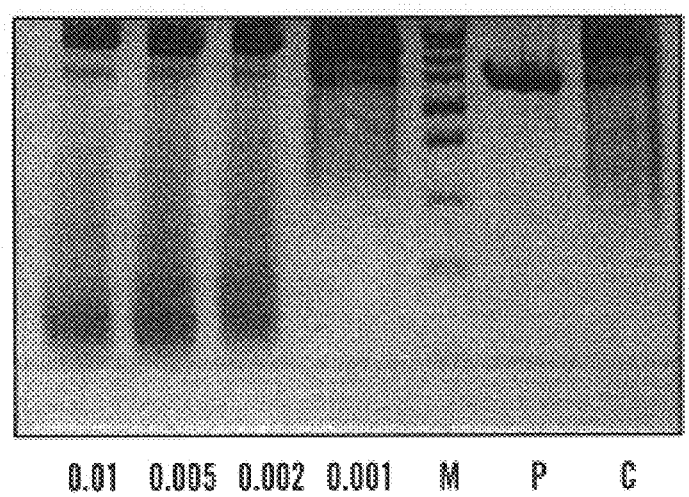

When r-AppA was incubated with trypsin, the enzyme protein was degraded at the ratios above 0.01 and was invisible at the ratio of 0.025. There was a major band of approximately 28 kDa, with several other bands between this band and the intact protein in the three low ratios of trypsin. However, that major band was clearly reduced and the other bands disappeared at the highest ratio of trypsin (FIG. 3A). There were many intermediary bands when the r-PhyA was incubated with various amounts of trypsin and there were at least three visible bands at the highest ratio of trypsin (FIG. 3B). A unique band of approximately 8.4 kDa was shown when r-AppA was incubated with pepsin at the ratio above 0.002 (FIG. 4A). On the other hand, proteolysis of r-PhyA by various amounts of pepsin resulted in many diffused and smearing bands, in addition to a major fragment of approximately 14 kDa (FIG. 4B).

Example 6

Figure 5A:
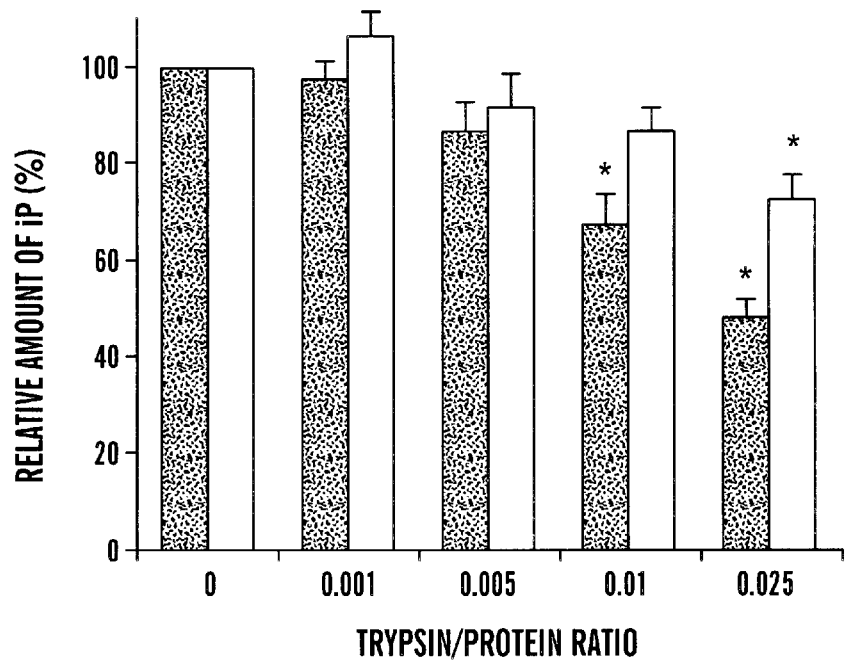
FIG. 5 shows the amounts of inorganic phosphorus (iP) released from soybean meal by r-PhyA and r-AppA incubated with different concentrations of trypsin (r=0.001, 0.005, 0.01, and 0.025, w/w) (FIG. 5A), or pepsin (r=0.001, 0.002, 0.005, and 0.01) (FIG. 5B). Symbols: r-AppA (■), r-PhyA (□). The results are the mean SEM from three independent experiments. * indicates statistical significance (P<0.01) versus untreated r-AppA or r-PhyA control.
Figure 5B:
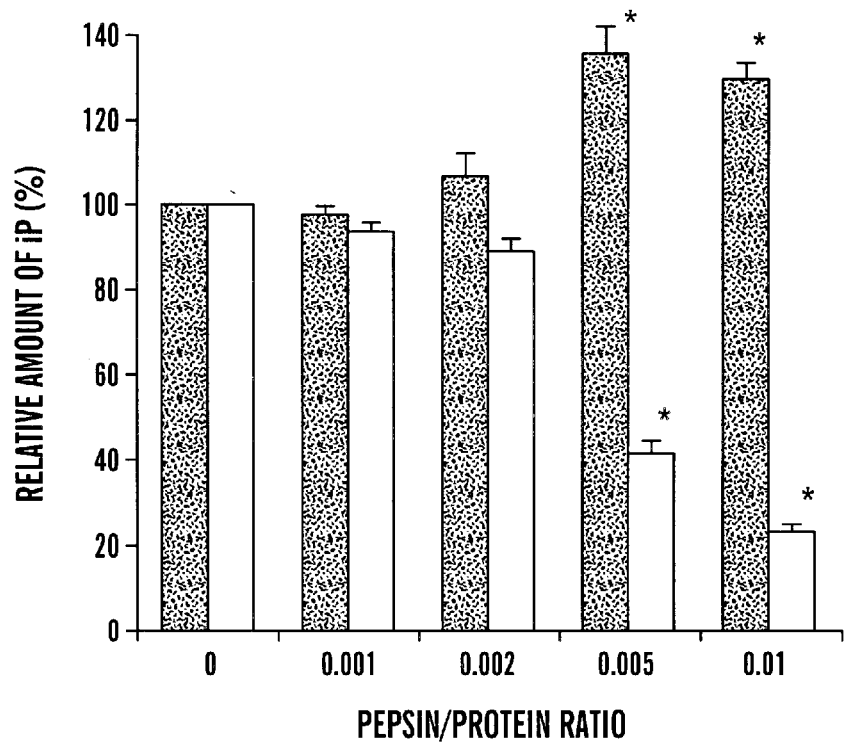

Effects of Proteolysis on Phytate-Phosphorus Hydrolysis by r-PhyA and r-AppA When r-AppA was incubated with soybean meal and different amounts of trypsin for 2 h at 37° C., the reduction in iP released from soybean meal was 3, 13, 34, and 52%, at the ratio of 0.001, 0.005, 0.01, and 0.025, respectively (FIG. 5A). Meanwhile, the reduction for r-PhyA at the same condition was 3, 6, 13, and 28%, respectively. Adding pepsin to r-AppA (ratio 0.005) and the soybean meal mixture resulted in approximately 30% increase in iP released from soybean meal, compared with the control (FIG. 5B). In contrast, the same treatments produced more than 50% reduction in iP release by r-PhyA.

To date, there have been no specific data on sensitivities of microbial phytases to trypsin and pepsin. In this study, two partially purified recombinant phytases were exposed to single protease digestions, and measured the effects of proteolysis on their residual activities and their capacity of releasing phytate phosphorus from soybean meal. These results have demonstrated that r-PhyA is more resistant to trypsin and less resistant to pepsin than r-AppA. The proteolytic patterns of these two phytases, shown by SDS-PAGE analysis, are also distinctly different. Presumably, these different susceptibilities to proteases between r-PhyA and r-AppA may be associated with their characteristics of primary amino acid sequence and peptide folding, because there is a low homology (~15%) of amino acid sequences between these two enzymes (17, 18). However, caution should be given in consideration of the molecular mechanism of phytase proteolysis, which is beyond the original scope of the present study. Recent progress in crystallization and (or) preliminary X-ray analysis of the phyA phytase (26) and an *E. coli* phytase (27) would help us in understanding the structural basis for their proteolytic responses.

Unexpectedly, r-AppA showed a 30% increase in residual phytase activity after pepsin digestion. Likewise, this enzyme also released 30% more iP from soybean meal in the presence of pepsin. From the SDS-PAGE analysis, r-AppA was clearly degraded into small peptides by pepsin along different periods of incubation. Likely, there may be potential pepsin resistant polypeptides with higher phytase activity than the intact r-AppA protein. Although the SDS-PAGE analysis did not offer us any specific information on such peptides, pepsin has been shown to convert natural or synthetic proteins in active polypeptides, such as converting porcine endothelin to active 21-residue endothelin (28). Pepsin may also modulate the structure and functions of certain proteins (29, 30). As mentioned above, the availability of the recent crystallization data on the phyA (26) and the E. coli phytases (27) would facilitate targeting site-directed mutageneses or deletions of the appA gene. Thereby, it may be possible to unveil the molecular mechanism for the increase of phytase activity of r-AppA associated with pepsin hydrolysis. In spite of the biochemical uncertainty of the pepsin resistant r-AppA peptides, this finding has a great nutritional implication. Because pepsin, a well described aspartic protease, is the major protease in the stomach (31), a pepsin resistant phytase polypeptides could allow us to supplement a low level of enzyme to the diets with sufficient activity. Thus, expense for use of dietary phytase in animal production will be reduced.

It is difficult to compare the activity levels of proteases used in the present study with those at the physiological conditions, because the in vivo concentrations of pepsin and trypsin have not been well described. An average trypsin activity of 20 to 25 U/mg of protein has been reported in the intestine of pig (32), which is much higher than the doses used herein. However, multiple levels of trypsin and pepsin were used, with 10 to 25 fold range. differences between the lowest and highest levels. In addition, the iP release from soybean meal by r-AppA or r-PhyA was measured in the presence of pepsin or trypsin, a simulated in vivo digestive condition. Although both r-AppA and r-PhyA were partially purified, all the data consistently point toward distinct responsive patterns of these two recombinant enzymes to pepsin and trypsin. Thus, this in vitro observation could be relevant to physiological conditions.

Example 7

Materials and Methods for Examples 8–12

Isolation and identification of phytase producing bacterium colonies. Colon contents were obtained from crossbreed Hampshire-Yorkshire-Duroc pigs (13 weeks of age) raised under confinement at Cornell University Swine Farm. These pigs were fed a practical corn-soybean meal diet. Immediately after the pigs were killed, the content of colon was removed by aseptic procedures and kept in anaerobic, sterile plastic bags. A 10 g sample was diluted with 190 ml of an anaerobic rumen fluid glucose medium in a 250 ml rubber-stoppered Erlenmeyer flask. The mixture was shaken vigorously for 3 min under a $CO_2$ atmosphere. Serial successive dilutions were made accordingly.

Diluted samples were cultured at 37° C. for 3 days in a modified rumen fluid-glucose-cellobiose-Agar medium containing insoluble calcium phytate (43, 44). Colonies with a clear zone were tested as a potential producer of intra and extracellular phytase activity. Phytase activity was measured using sodium phytate as a substrate (24). One phytase unit (PU) was defined as the activity that releases one $\mu$mole of inorganic phosphorus from sodium phytate per minute at 37° C. Acid phosphatase activity was assayed using p-nitrophenyl phosphate (P-NPP) as a substrate according to the manufacturer instructions (Sigma, St Louis, Mo.). Identification of the selected colony was conducted in the Diagnostic Laboratory of Cornell Veterinary College (Ithaca, N.Y.). Morphological and physiological characteristics of the isolated colony were determined by standard procedures.

DNA amplification and sequencing Because the colony that produced the highest acid phosphatase and phytase activities was identified as an E. coli strain, primers derived from the DNA sequence of E. coli pH 2.5 acid phosphatase gene (appA, GeneBank Accession number 145283) (18) were used to isolate the gene. Primers Pf1 [forward: 1–22]:

5'-TAAGGAGCAGAAACAATGTGGT-3' (SEQ. ID. No. 4), E2 [forward: 254–264]:

5'-GGAATTCCAGAGTGAGCCGGA-3' (SEQ. ID. No. 5), and K2 [reverse: 1468–1491]:

5'-GGGGTACCTTACAAACTGCACG-3' (SEQ. ID. No. 6) were synthesized at the Cornell University Oligonucleotide Synthesis Facility. The whole sequence and the coding region were amplified using [Pf1-K21 and [E2-K2] primers, respectively. The PCR reaction mixture (100 $\mu$l,) contained 500 ng of genomic DNA as template, 100 pmole of each primer, 5 U of AmpliTaq DNA polymerase (Perkin Elmer, Norwalk, Conn.), 10 mM Tris-HCl pH 8.3, 5 0 mM KCl, 12.5 mM MgC 12, and 200 $\mu$M each dNTPs (Promega, Madison, Wis.). The reaction was performed by the GeneAmp PCR system 2400 (Perkin Elmer). The thermal program included 1 cycle at 94° C. (3 min), 30 cycles of [94° C. (0.8 min), 54° C. (1 min) and 72° C. (2 min)] and 1 cycle at 72° C. (10 min). Amplified PCR products were resolved by 1% low melting agarose (Gibco BRL, Grand Island, N.Y.) gel electrophoresis. A gel slice containing the expected size band was excised and DNA was eluted with GENECLEAN II kit (Bio101, Vista, Calif.). The PCR products were sequenced at the Cornell University DNA Service Facility using Taq Cycle automated sequencing with Dye Deoxy terminators (Applied Biosystems, Forster City, Calif.). Sequencing experiments were performed five times and the deduced amino sequence was aligned with other acid phosphatases and phytases using the Multi-align Program CLUSTAL BLAST (45). The two identified PCR fragments [Pf1-K2] and [E2-K2] were described, respectively, as appA2 and appA2 in the following text. For comparative purposes, the appA gene was amplified from E. coli BL21 (DE3) using the primers [E2-K2]. The PCR reactions and the resulting fragments were processed as described above.

Subcloning and construction of expression vectors. The PCR products [E2-K2] and [Pf1-K2] were cloned into pGEM® T-easy vector (Promega) according to the manufacturer instructions and transformed into TOP10F to screen for positive colonies. The isolated appA2 and appA fragments were inserted into the pPICZ$\alpha$A (Invitrogen, San Diego, Calif.) at the EcoRI and KpnI sites, as described by the manufacturer instruction. The constructs were transformed into TOP10F cells which were plated on LB medium containing 25 $\mu$g zeocin/ml. The positive colonies were then grown to prepare DNA for transformation.

Yeast transformation and expression. Pichia pastoris strain X33 (Invitrogen) were grown in YPD medium and prepared for transformation, according to the manufacturer instructions. Two $\mu$g of plasmid DNA was linearized using Bg/II and then transformed into Pichia by electroporation. After incubation for 3 h at 30° C. in 1 M sorbitol without agitation, cells were plated in YPD-zeocin agar medium to screen integration of the transformed gene into the 5' AOX1 region of the host chromosomal DNA. After 2 days, transformants were incubated in minimal media with glycerol (GMGY medium) for 24 h. After the culture reached a density of about 2.5 $10^8$ cells/ml ($OD_{600}$=5), the cells were spun down (3500 g, 5 min) and then suspended in 0.5% methanol medium (GMMY) to induce the phytase gene expression.

RNA quantification. Total RNA was extracted from the appA2 transformants at different times after induction. The RNA was separated in 1% formaldehyde-agarose gel, transferred onto Hybond N+ membrane (Amersham Pharmacia Biotech, Piscataway, N.J.) by capillary blotting and UV cross-linked for 2 min. The membrane was then pre-hybridized for 4 h at 42° C. The probe was the appA2 [E2-K2] PCR fragment, and was labeled with [$\alpha$-$^{32}$P]-dCTP (DuPont, Boston, Mass.) using Ready-To-Go TM DNA Labeling Beads (Amersham Pharmacia Biotech). The membrane was hybridized with the probe overnight at 42° C., and washed three times for 20 min at 25° C. and twice at 50° C. in 2×SSC (0.15 M NaCl, 0.015 M sodium citrate), 1% sodium dodecyl sulfate (SDS), and finally twice at 50° C. in 0.2×SSC, 0.1% SDS. The autoradiogram was produced by exposing the membrane to an intensifying screen of BAS-III FUJI Imaging plate (Fuji, Japan) for 10 h and quantified using a Bio-Imaging Analyzer (Kohshin Graphic Systems, Fuji, Japan). Results were normalized by the relative levels of 18S rRNA.

Purification of the expressed enzymes. All operations were carried out at 4° C. Both expressed r-appA and r-appA2 enzymes, and the r-phyA phytase expressed in A. niger (kindly provided by BASF, Mt. Olive, N.J.), were suspended in 50 mM Tris-HCl, pH 7 with 25% saturation of ammonium sulfate. The suspension was then centrifuged at 25,000 g for 20 min. The supernatant was mixed with 75% saturated ammonium sulfate under agitation for 12 h, and the mixture was centrifuged at 25,000 g for 20 min. The pellet was then suspended in 10 ml 25 mM Tris-HCl, pH 7 and dialyzed overnight against the same buffer. The dialyzed sample was loaded onto a DEAE-Sepharose column (Sigma) equilibrated with 25 mM Tris-HCl, pH 7. After the column was washed with 200 ml of the same buffer, the bound phytase was eluted with 1 M NaCl in 25 mM Tris-HCl, pH 7. Three fractions exhibiting the highest phytase and acid phosphatase activities were pooled and dialyzed against 25 mM Tris-HCl, pH 7.5 overnight for the following studies.

Electrophoretic analysis. Protein concentration was measured by the Lowry's method (21). Non-denaturing gel electrophoresis and SDS-PAGE (15%) were performed as described by Laemmli (22). Proteins in SDS-PAGE were stained with Coomassie brillant blue R-250. Acid phosphatase or phytase activity in bands of the non-denaturing gel was detected as described previously (17). After electrophoresis, the gel was incubated for 20 min at 25° C. in 0.2% α-19 naphtylphosphate (or sodium phytate), 0.1% Fast Garnet GBC salts, 1 mM CaC12, and 0.5 M Tris-HCl buffer pH 7.0.

Deglycosylation of the enzymes. Deglycosylation of r-appA2 was done using 0.3 IU of endoglycosidase $H_f$ (Endo $H_f$) for 4 h at 7° C. according to the manufacturer instructions (New England Biolabs, Beverly, Mass.). The deglycosylated proteins were analyzed in a 15% SDS-PAGE as described above.

Enzyme properties and hydrolysis of phytate phosphorus in soybean meal. Phytase activity at different pH was determined at 33° C., using three different buffers. The temperature optimum for each enzyme was determined at its optimal pH. The $K_m$ and $V_{mas}$, values for r-appA2 and r-appA were determined at the optimal pH of each enzyme and 37° C. Hydrolysis of phytate phosphorus by r-appA2 was compared with that of r-appA and r-phyA. Different amounts of the purified enzymes were incubated with 1 g soybean meal in a 5 mL buffer (10 mM HCl or 0.2 M citrate) at their respective optimal pH (2.5 for r-appA, 3.5 for r-appA2, and 5.5 for r-phyA) at 37° C. for 2 h. The released inorganic phosphorus was determined as previously described (25). Thermostabilities of these three enzymes were compared. Each of the enzymes (2 mg/ml) was diluted 1:200 in 0.2 M sodium citrate, pH 5.5, and incubated for 20 min at 25, 37, 55, 65, 80 and 100° C. The samples were placed on ice for 30 min and the remaining phytase activity was measured at 37° C.

Statistical test employed The Mann-Withney U-test was used for all the statistical evaluations (46).

Example 8

Bacterial Colony Screening and Identification

A total of 93 colonies were isolated. Over 70 colonies had intracellular phytase activity less than 500 U/g protein, and 6 colonies had activities greater than 1,000 U/g protein. Colony 88 demonstrated the highest phytase activity (2,927 U/g protein), with an acid phosphatase activity (1,391 U/g protein). Thus, it was chosen for further experiments. The production of phytase and acid phosphatase activities by the colony was greater in Sweet E than LB broth and greater at anaerobic than aerobic conditions. Subsequently, the colony was identified as a gram negative *E. coli*. This was confirmed, in particular, by the substrate fermentation profile.

Example 9

Cloning and Sequencing of the Pig *E. coli* appA2 Gene

A 1482 bp (whole) and a 1241 bp (coding region) fragments were amplified from the genomic DNA of Colony 88 (FIG. 6). Except for the *E. coli* appA gene and the Bacillus phytase gene, no significant sequence homologies were found in the GenPro databank (version 61), GeneBank or EMBL databases using BLAST program. The whole nucleotide sequence had 47 and 95% homology with the Bacillus sp. DS 11 phytase gene (GeneBank accession number 3150039) and *E. coli* appA, respectively. In spite of such a high nucleotide sequence homology, there were distinct differences between appA and appA2 and their encoding polypeptides. First, seven amino acids were different in the deduced peptide sequences: one in the signal peptide, L4F; six in the coding region, S102P, P195S, S197L, K202N, K298M, and T299A. Second, the 73 bp untranslated region, located between the lead sequence and coding region, was shorter by 6 bp than that of appA. However, the three putative N-glycosylation sites were still located in the coding region at the same place. The DNA fragment was sequenced for five times to verify these differences. Compared with phyA, appA2 had only a 19% of amino acid sequence homology. The sequence has been transmitted to GeneBank data library with the accession number 250016.

Example 10

Expression of appA2 in *Pichia Pastoris*

Figure 7:
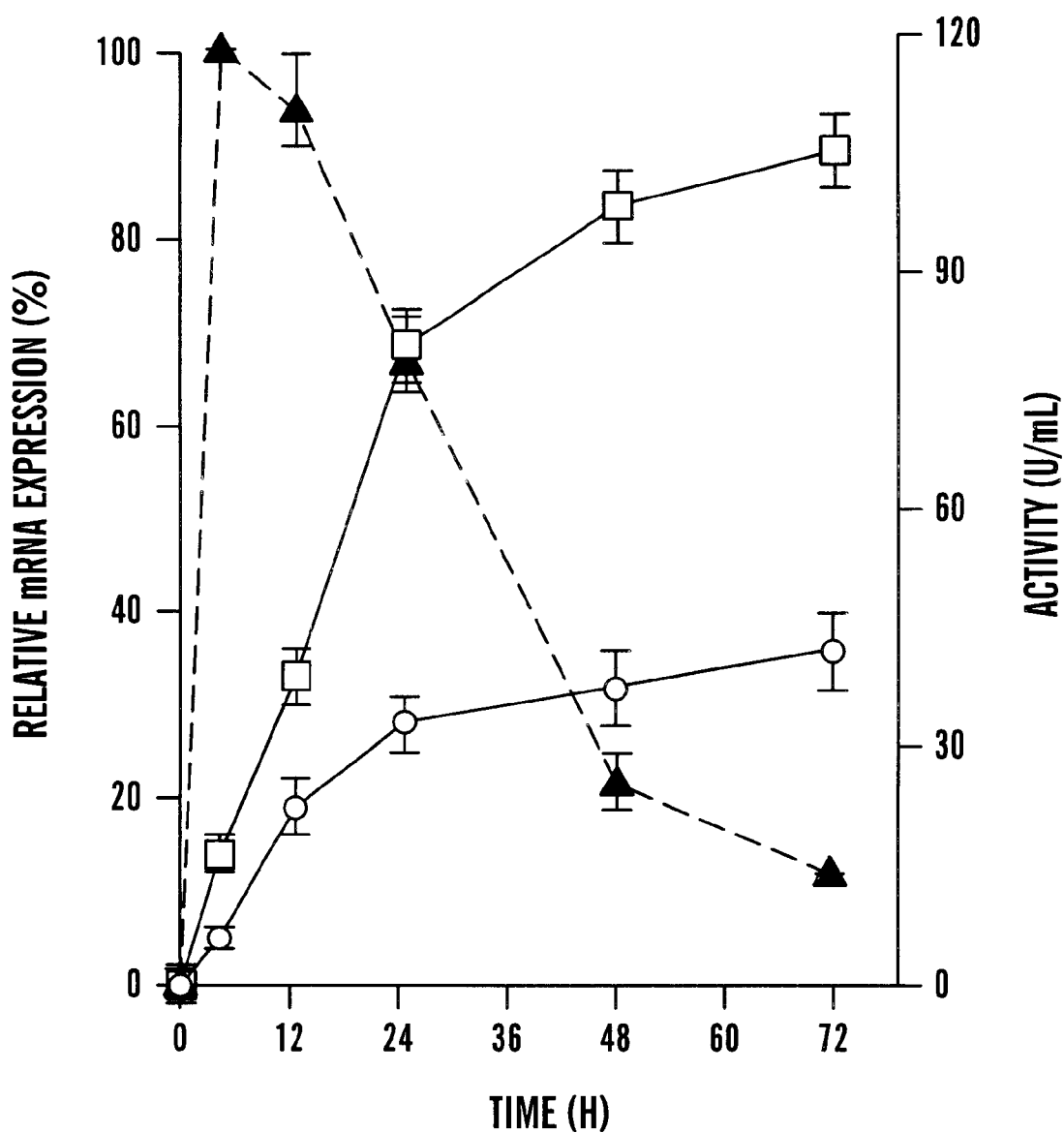
FIG. 7 is a time course of extracellular phytase (□) and acid phosphatase (○) activities, and CIPPA2 mRNA expression (▲) in Pichia pastoris transformed with appA2 after induction. Results are expressed as the mean±SEM from three experiments.
Figure 8A:
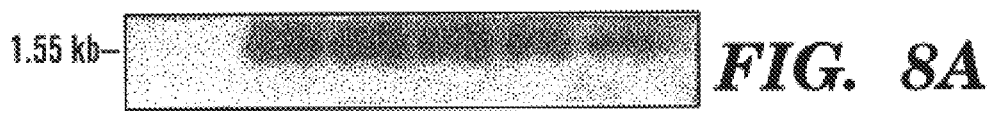
FIG. 8 shows a northern blot analysis of appA2 mRNA expression in *Pichia pastoris* transformed with appA2 after induction (FIG. 8A). Hybridization was realized using [α-$^{32}$P] labeled appA2 as a probe. Twenty μg of total RNA was loaded per lane. Panel B represents the equal RNA loading visualized by the yeast rRNA under UV.
Figure 8B:
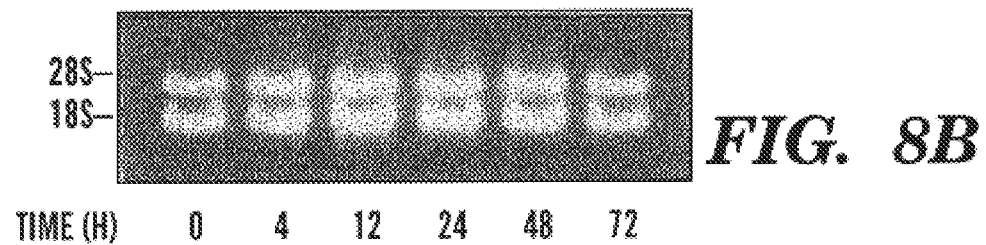

A total of 42 transformants were analyzed for phytase and acid phosphatase activities at various intervals. Three days after methanol induction, 13 transformants produced phytase activity from 18 to 114 U/mL of medium and acid phosphatase activity from 7 to 42 U/mL. Meanwhile, 22 appA transformants expressed phytase activity from 25 to 130 U/mL and acid phosphatase activity from 59 to 85 U/mL. The appA2 transformant that demonstrated the highest activities was used in the expression time course (FIG. 7) and other studies. The appA2 mRNA level reached the peak at 4 h (FIGS. 7 and 8), remained high until 12 h, and thereafter declined significantly. No appA2 mRNA signal was detected in the control cells. Both the extracellular phytase and acid phosphatase activities produced by the transformant increased sharply between 0 and 24 hours. Thereafter, the acid phosphatase activity remained nearly unchanged while phytase activity increased much less over time than that at the earlier phase.

Example 11

Characterization of the Purified Enzymes

The specific phytase activity of the purified r-appA2, r-appA, and r-phyA enzymes was 28.9, 30.7, and 19.8 U/mg protein, respectively. The purified r-appA2 demonstrated a higher affinity for sodium phytate than pNNP, as shown by the $K_m$ and $V_{max}$ values (Table 1). When sodium phytate was used as the substrate, the pH curve was significantly different among the three enzymes.

TABLE 1

Kinetic parameters of the purified r-appA
and r-appA2 expressed in *Pichia pastoris*

|  | r-appA | r-appA2 |
| --- | --- | --- |
| $K_m$, mM |  |  |
| Sodium phytate | 1.03 | 0.66 |
| p-NPP | 2.26 | 1.43 |
| $V_{mzx}$, $\mu$mole min$^{-1}$ mg$^{-1}$ |  |  |
| Sodium phytate | 89 | 117 |
| p-NPP | 310 | 340 |

Figure 9:
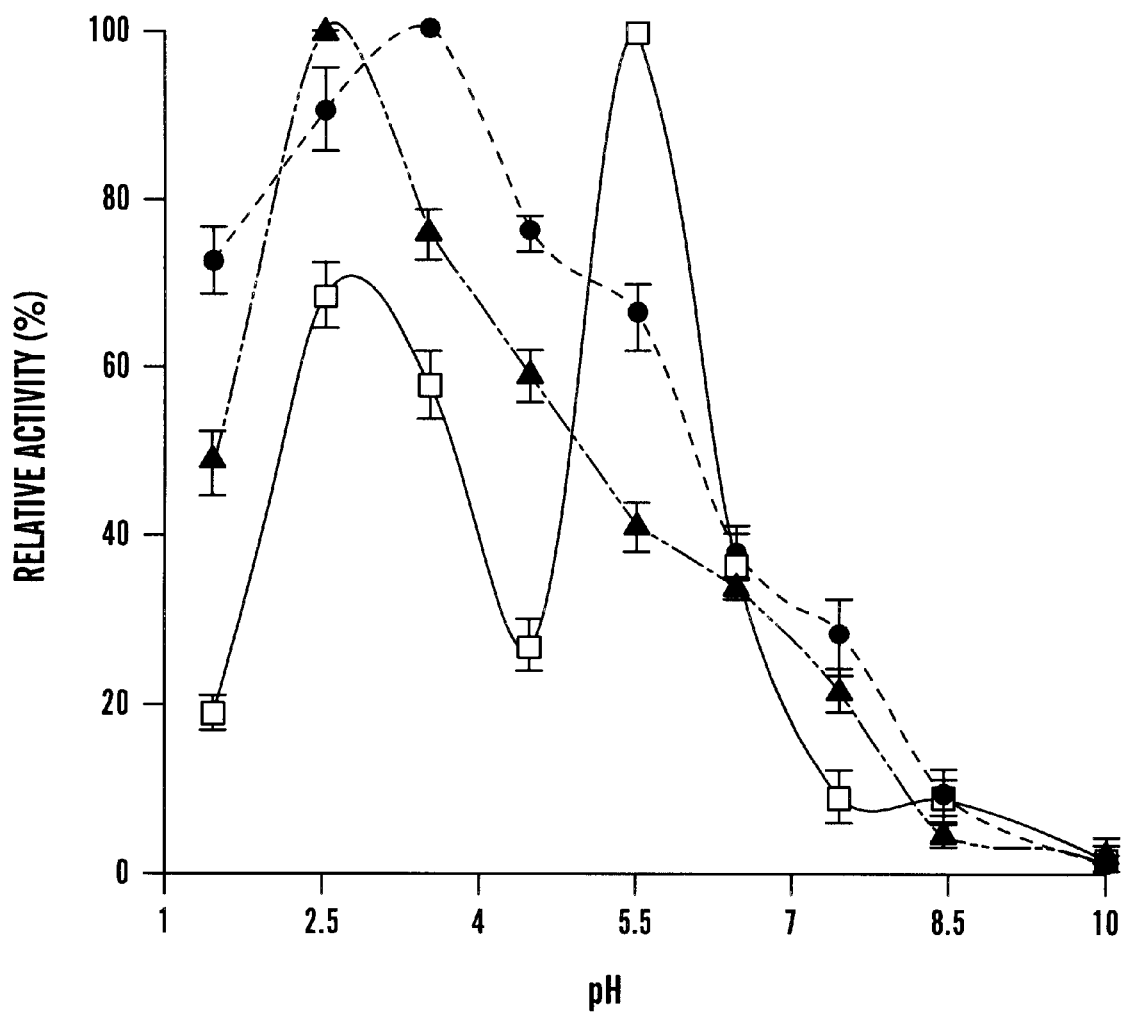
FIG. 9 shows the pH dependence of the enzymatic activity at 37° C. of the purified r-appA2 (●), r-appA (▲), and r-phyA (□) with sodium phytate as the substrate. Buffers: pH 1.5–4.5, 0.2M glycine-HCl; pH 5.5–7.5, 0.2 M citrate; pH 8.5–11, 0.2 M Tris-HCl. Results are expressed as the mean SEM from three experiments.
Figure 10:
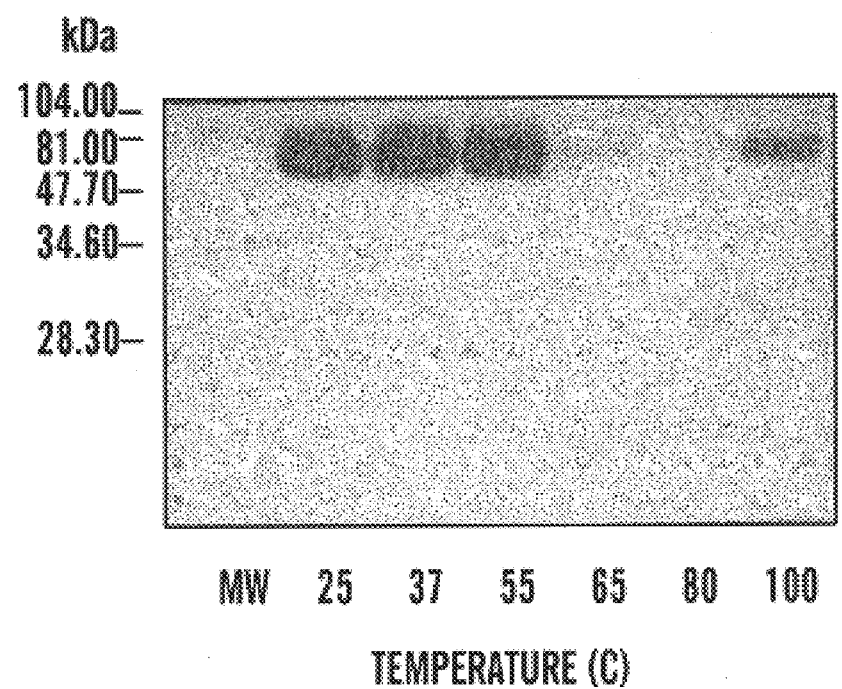
FIG. 10 shows a non-denaturing gel (15%) electrophoresis analysis of the remaining acid phosphatase activity of r-appA2 after incubated at different temperatures for 20 min. After the heat treatment, the samples were put on ice for 5 min before being loaded onto the gel (200 μg protein/lane).
Figure 11:
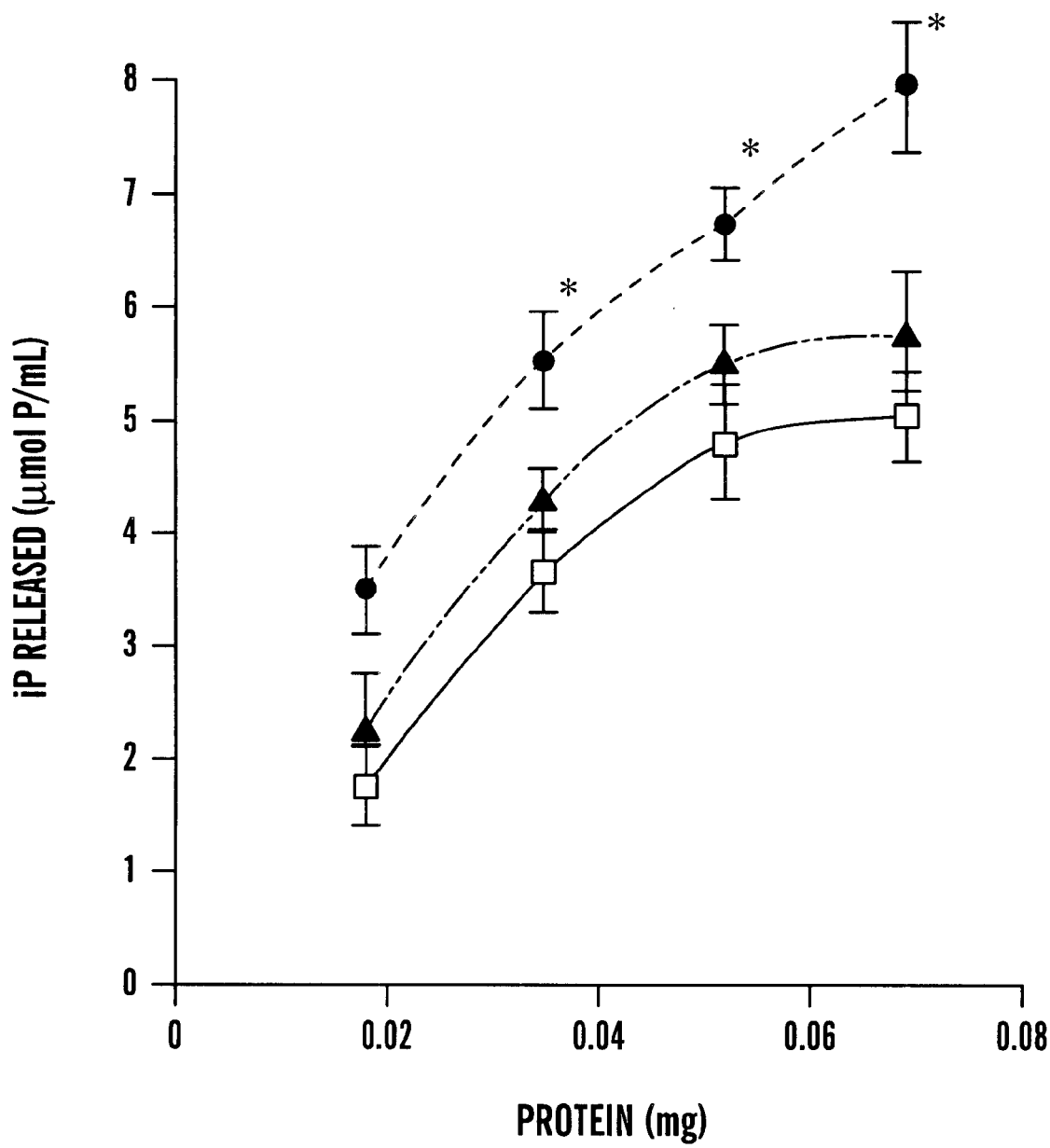
FIG. 11 shows the hydrolysis of phytate phosphorus in soybean meal by different amounts (100, 300, 600, and 900 PU) of purified r-appA2 (●), r-appA (▲), and r-phyA (□) enzymes. * indicates significant differences (P<0.05) between r-appA2 and other two enzymes. Results are expressed as the mean±SEM from three experiments.

The pH optimum was between 2.5 and 3.5 for r-appA2, 2.5 for r-appA, and 2.5 and 5.5 for r-phyA phytase (FIG. 9). However, the two *E. coli* enzymes demonstrated the same pH optimum (2.5) for the substrate pNNP. In addition, both r-appA and r-appA2 had the same temperature optimum (55° C.) which was slightly lower than that of r-phyA. These two enzymes also had very similar thermostabilities of phytase activity which were slightly higher between 37 and 60° C. and lower between 65 and 100° C. than that of r-phyA. The acid phosphatase activity of r-appA2 that remained after different temperature treatments was shown in the non-denaturing gel, as a unique band of 71 kDa (FIG. 10). The activity was largely or completely lost at 65 or 80° C., but somehow recovered partially at 100° C. When the three purified recombinant enzymes were incubated with soybean meal, r-appA2 protein released significantly more phosphorus from phytate than the other two enzymes (FIG. 11).

Example 12

Effects of Deglycosylation on Enzyme Properties

After the three purified enzymes were treated with β-mercaptoethanol and Endo $H_f$, more than 90% of their activities for both sodium phytate and pNNP were lost. But, Endo $H_f$ alone had no significant effect on their catalytic activities. Deglycosylation of r-appA2 resulted in a single band with an apparent Mr of 46.3 kDa from three distinguished bands for the glycosylated forms with apparent Mr of 50.5, 53 and 56 kDa. This gave a range of glycosylation for r-appA2 between 8.3 and 17.3%.

In the above examples, a phytase-producing *E. coli* strain was isolated from the pig colon content. Using primers based on the *E. coli* pH 2.5 acid phosphatase gene (appA) described by Dassa et al. (18), a 1489 bp DNA fragment was amplified from the genomic DNA of the strain. This fragment, designated as appA2 (SEQ. ID. No. 9), encodes a protein of 433 amino acids (SEQ. ID. No. 1) with 3 putative N-glycosylation sites. The deduced peptide contains both the N-terminal motif (RHGXRXP, position: 38–44) (SEQ. ID. No. 7) and the C-terminal motif (HD, position: 325–326), characteristic for histidine acid phosphatases (8). In addition, there is a lead sequence of 30 amino acids (SEQ. ID. No. 8) and an untranslated region of 73 bp. Among the available sequence databases, only the *E. coli* appA pH 2.5 acid phosphatase and the Bacillus sp. DS 11 phytase genes share some homology with appA2 (95% and 47% in nucleotide sequence, respectively). In spite of the high homology between appA and appA2, there are distinct differences between these two genes and their respective proteins. First, seven amino acids differ between the two deduced polypeptide sequences: one within the signal peptide and six in the coding region. Second, the 73 bp untranslated region between the lead sequence and the coding region was shorter by 6 bp than that of appA. All those differences have been confirmed by five repetitive nucleotide sequencing analysis.

More importantly, when these two genes are transformed into the same host, *Pichia pastoris*, the expressed proteins r-appA and r-appA2 show differently biochemical characteristics. Although both exhibit the same pH optimum of 2.5 for pNNP, r-appA2 has a broad pH optimum between 2.5 and 3.5 while r-appA had it at 2.5 for sodium phytate. Compared with r-appA, the r-appA2 has a higher affinity for both substrates, as shown by the lower $K_m$ and higher $V_{max}$ values, and releases more phosphorus from phytate in soybean meal in vitro. Thus, the catalytic function of r-appA2, towards phosphorus hydrolysis from phytate or phosphate, seems to be better than that of r-appA. Apparently, the six amino acid exchanges in the polypeptide may not be not just a polymorphism of the enzyme, but rather responsible for the observed kinetic differences. Thus, it seems reasonable to state that the appA2 is a different gene from appA, although a more defined structural analysis is needed to elucidate the relationship between specific amino acid exchanges and functional alterations of these two enzymes. It will be necessary to produce the crystal of both enzymes first for future structural studies (27).

Previously, several *E. coli* enzymes have been reported to hydrolyze pNNP or sodium phytate (18, 19, 39–41). Greiner et al. (39) characterized two *E. coli* phytases (P1 and P2). They found that the purified *E. coli* phytase P2 shares a great identity with the *E. coli* pH 2.5 acid phosphatase in the N-terminal sequence, chemical properties, and kinetics. Thus, they suggested that these two enzymes might be the same protein and the *E. coli* pH 2.5 acid phosphatase should better be regarded as a phytase. Indeed, both r-appA acid phosphatase and r-appA2 are not only able to hydrolyze phytate in the pure chemical form or in the natural food, but also have a higher affinity for sodium phytate than pNNP. Therefore, these two enzymes could be classified as phytases.

Compared with the purified phytase P2 (39), r-appA2 has the same optimum temperature (55° C.) and similar molecular mass after deglycosylation (46.3 kDa). Based on the SDS-PAGE and non-denaturing gel analyses, the protein is also monomeric. However, r-appA2 has a more acidic pH optimum (2.5 to 3.5 vs. 4.5 for P2) and contains 8 to 14% of sugar moieties because of the N-glycosylation in Pichia. Deglycosylation of r-appA2 with Endo $H_f$ reduces the molecular size but has a minimal effect on its activity. In contrast, when the protein is incubated with P-mercaptoethanol and Endo Hf, the phytase and acid phosphatase activities of r-appA2 are considerably reduced. This indicates that disulfide bonds are required for its phytase activity as previously shown for the A. ficuum phytase (47).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

References

The following references which were cited herein, are hereby incorporated by reference into this application:
1. Pallauf, J. et al., *Arch Tierernahr*, 50, 301–319 (1997).
2. Greiner, R. et al., *Arch. Biochem. Biophys.*, 303, 107–113 (1993).
3. Kim, Y. et al., *Enz. Microbiol. Technol.*, 22, 2–7 (1998).
4. Shieh, T. R. et al., *Appl. Microbiol.*, 16,1348–1351 (1968).
5. Mitchell, D. B. et al., *Microbiol.*, 143, 245–252 (1997).
6. Pasamontes, L. et al., *Appl. Environ. Microbiol.*, 63, 1696–1700 (1997).
7. Barberic, S. et al., *J Biol. Chem.*, 259, 878–883 (1984).
8. Wodzinski, R. J. et al., *Adv. Appl. Microbiol.*, 42, 263–302 (1996).
9. Liu, B. L. et al., *Enz. Microbiol. Technol.*, 22, 415–424 (1998).
10. Harper, A. F. et al., *J. Anim. Sci.*, 75,3174–86 (1997).
11. Lei, X. G. et al., *J. Anim. Sci.*, 71, 3359–3367 (1993a).
12. Lei, X. G. et al., *J. Anim. Sci.*, 71, 3368–3375 (1993b).
13. Jongloed, A. W. et al., *J. Anim. Sci.*, 70, 1159–1168 (1992).
14. Stahl, C. H. et al., *J. Anim. Sci.*, 77, (In press) (1999).
15. Jongbloed, A. W. et al., *Vet. Q.*, 19, 13 0–134 (1997).
16. Skoglund, E. et al., *Can. J. Anim. Sci.*, 78, 175–180 (1998).
17. Van Hartingsveldt, W. et al., *Gene*, 127, 87–94 (1993).
18. Dassa, J. et al., *J. Bacteriol.*, 172, 5497–5500 (1990).
19. Pradel, E. et al., *J. Bacteriol.*, 170, 49 16–4923 (1988).
20. Ostanin, K. et al., *J. Biol. Chem.*, 267, 22830–22836 (1992).
21. Lowry, O. H. et al., *J. Biol. Chem.*, 193, 265–275 (1951).
22. Laemmli, U. K., *Nature*, 227, 680–685 (1970).
23. Sherton, C. C. et al., *J. Biol. Chem.*, 249, 2258–2262 (1974).
24. Piddington, C. S. et al., *Gene*, 133, 55–62 (1993).
25. Chen, P. S. et al., *Anal. Chem.*, 28, 1756–1758 (1956).
26. Kostrewa, D. et al., *Nature Stru. Biol.*, 4, 185–189 (1997).
27. Jia, Z. et al., *Acta Crystallogr. D. Biol. Crystallogr.*, 54, 647–649 (1998).
28. Takaoka, M. et al., *Biochem. Biophys. Res. Commun.*, 166,436–442 (1990).
29. Fruton, J. S., *Adv. Exp. Med. Biol.*, 95,131–140 (1977).
30. Savoie, L. et al., *Plant Foods Hum. Nutr.*, 40, 233–242 (1990).
31. Wiesemuller, W. et al., *Arch. Tierenahr.*, 40, 689–693 (1990).
32. Tivey, D. R. et al., *In Digestive physiology in pigs*, pp. 140–143, EAAP No. 88.
33. Han, Y. M. et al., *J. Anim. Sci.*, 76,2649–2656 (1998).
34. Lolas, M. et al., *J. Food Sci.*, 42, 1094–1097 (1977).
35. Reddy, N.L. et al., *Adv. Food Res.*, 28,1–92 (1982).
36. Pasamontes, L. et al., *Biochem. Biophys. Acta*, 1353, 217–223 (1997).
37. Dvorak H. F. et al., *Biochemistry*, 6, 1743–1751 (1967).
38. Dassa, E. et al., *J. Biol. Chem.*, 257, 6669–6676 (1982).
39. Greiner, R. et al., *Arch. Biochem. Biophys.*, 303, 107–113 (1993).
40. Greaves, M. P. et al., *Biochem. Biophys. Acta*, 132, 412–418 (1967).
41. Kerovuo, J. et al., *Appl. Environ. Microbiol.*, 64, 2079–85 (1998).
42. Kim, Y. O. et al., *FEMS Microbiol. Lett.*, 162, 185–191 (1998).
43. Butine, T. J. et al., *Appl,. Environ. Microbiol.*, 55, 1112–1116 (1989).
44. Robinson, L. M. et al., *appA. Environ. Microbiol.*, 48, 964–969 (1984).
45. Altschul, S. F. et al., *J. Mol. Biol.*, 215, 403–410 (1990).
46. Zan, G. H., *In Biostatistical. Analysis*, pp. 109–114, Prentice-Hall, Englewood Cliffs, N.J. (1974).
47. Ullah, A. H. J. et al., *Biochem. Biophys. Res. Commun.*, 227, 311–317 (1996).
48. Bitter et al., *Meth. Enzymol.* 153, 516–44 (1987).
49. Struhl et al., *Proc. Nat'l Acad. Sci. USA* 76, 1035–39 (1979).
50. Powels et al., *Cloning Vectors. I–IV, et seq.* Elsevier, (1985).
51. Sakai et al., *Biotechnology* 9, 1382–85 (1991).
52. Stetler et al., *Biotechnology* 7, 55–60, (1989).
53. Hitzeman et al., *J. Biol. Chem.* 255, 2073 (1980).
54. Hess et al., *J. Adv. Enzyme Reg.* 7, 149 (1968).
55. Holland et al., *Biochem.* 17, 4900, (1978).
56. Russell et al., *J. Biol. Chem.* 258, 2674 (1982).
57. Beier et al., *Nature* 300, 724 (1982).
58. Kurjan, et al., *Cell* 30, 933–43 (1982)
59Hinnen et al., *Proc. Natl. Acad. Sci. USA* 75, 1929 (1978).

What is claimed is:

1. An isolated AppA2 polypeptide having improved phytase activity and having an amino acid sequence as shown in SEQ. ID No. 1.

2. The isolated polypeptide according to claim 1, wherein the polypeptide is expressed in yeast.

3. The isolated polypeptide according to claim 2, wherein the yeast is *Pichia pastoris*.

4. The isolated polypeptide according to claim 2, wherein the yeast is *Saccharomyces cerevisiae*.

5. The isolated polypeptide according to claim 1, wherein the polypeptide is encoded by a recombinant gene comprising:
- a promoter;
- a coding region encoding the polypeptide according to claim 1; and
- a terminator.

6. An improved animal feed comprising the polypeptide according to claim 1.

* * * * *

SEQUENCE LISTING

```
<160> NUMBER OF SEQ ID NOS: 9

<210> SEQ ID NO 1
<211> LENGTH: 433
<212> TYPE: PRT
<213> ORGANISM: Escherichia coli
<220> FEATURE:
```

```
<221> NAME/KEY: UNSURE
<222> LOCATION: (433)
<223> OTHER INFORMATION: Xaa at position 433 in this sequence is unknown

<400> SEQUENCE: 1

Met Lys Ala Ile Leu Ile Pro Phe Leu Ser Leu Ile Pro Leu Thr
  1               5                  10                  15

Pro Gln Ser Ala Phe Ala Gln Ser Glu Pro Glu Leu Lys Leu Glu Ser
             20                  25                  30

Val Val Ile Val Ser Arg His Gly Val Arg Ala Pro Thr Lys Ala Thr
         35                  40                  45

Gln Leu Met Gln Asp Val Thr Pro Asp Ala Trp Pro Thr Trp Pro Val
     50                  55                  60

Lys Leu Gly Trp Leu Thr Pro Arg Gly Gly Glu Leu Ile Ala Tyr Leu
 65                  70                  75                  80

Gly His Tyr Gln Arg Gln Arg Leu Val Ala Asp Gly Leu Leu Ala Lys
                 85                  90                  95

Lys Gly Cys Pro Gln Pro Gly Gln Val Ala Ile Ile Ala Asp Val Asp
                100                 105                 110

Glu Arg Thr Arg Lys Thr Gly Glu Ala Phe Ala Ala Gly Leu Ala Pro
            115                 120                 125

Asp Cys Ala Ile Thr Val His Thr Gln Ala Asp Thr Ser Ser Pro Asp
130                 135                 140

Pro Leu Phe Asn Pro Leu Lys Thr Gly Val Cys Gln Leu Asp Asn Ala
145                 150                 155                 160

Asn Val Thr Asp Ala Ile Leu Ser Arg Ala Gly Gly Ser Ile Ala Asp
                165                 170                 175

Phe Thr Gly His Arg Gln Thr Ala Phe Arg Glu Leu Glu Arg Val Leu
                180                 185                 190

Asn Phe Ser Gln Leu Asn Leu Cys Leu Asn Arg Glu Lys Gln Asp Glu
                195                 200                 205

Ser Cys Ser Leu Thr Gln Ala Leu Pro Ser Glu Leu Lys Val Ser Ala
    210                 215                 220

Asp Asn Val Ser Leu Thr Gly Ala Val Ser Leu Ala Ser Met Leu Thr
225                 230                 235                 240

Glu Ile Phe Leu Leu Gln Gln Ala Gln Gly Met Pro Glu Pro Gly Trp
                245                 250                 255

Gly Arg Ile Thr Asp Ser His Gln Trp Asn Thr Leu Leu Ser Leu His
                260                 265                 270

Asn Ala Gln Phe Tyr Leu Leu Gln Arg Thr Pro Glu Val Ala Arg Ser
                275                 280                 285

Arg Ala Thr Pro Leu Leu Asp Leu Ile Met Ala Ala Leu Thr Pro His
    290                 295                 300

Pro Pro Gln Lys Gln Ala Tyr Gly Val Thr Leu Pro Thr Ser Val Leu
305                 310                 315                 320

Phe Ile Ala Gly His Asp Thr Asn Leu Ala Asn Leu Gly Gly Ala Leu
                325                 330                 335

Glu Leu Asn Trp Thr Leu Pro Gly Gln Pro Asp Asn Thr Pro Pro Gly
                340                 345                 350

Gly Glu Leu Val Phe Glu Arg Trp Arg Leu Ser Asp Asn Ser Gln
                355                 360                 365

Trp Ile Gln Val Ser Leu Val Phe Gln Thr Leu Gln Gln Met Arg Asp
    370                 375                 380

Lys Thr Pro Leu Ser Leu Asn Thr Pro Pro Gly Glu Val Lys Leu Thr
```

-continued

```
        385                 390                 395                 400
Leu Ala Gly Cys Glu Glu Arg Asn Ala Gln Gly Met Cys Ser Leu Ala
                    405                 410                 415

Gly Phe Thr Gln Ile Val Asn Glu Ala Arg Ile Pro Ala Cys Ser Leu
            420                 425                 430

Xaa

<210> SEQ ID NO 2
<211> LENGTH: 21
<212> TYPE: DNA
<213> ORGANISM: Escherichia coli

<400> SEQUENCE: 2
ggaattccag agtgagccgg a                                              21

<210> SEQ ID NO 3
<211> LENGTH: 22
<212> TYPE: DNA
<213> ORGANISM: Escherichia coli

<400> SEQUENCE: 3
ggggtacctt acaaactgca cg                                             22

<210> SEQ ID NO 4
<211> LENGTH: 22
<212> TYPE: DNA
<213> ORGANISM: Escherichia coli

<400> SEQUENCE: 4
taaggagcag aaacaatgtg gt                                             22

<210> SEQ ID NO 5
<211> LENGTH: 21
<212> TYPE: DNA
<213> ORGANISM: Escherichia coli

<400> SEQUENCE: 5
ggaattccag agtgagccgg a                                              21

<210> SEQ ID NO 6
<211> LENGTH: 22
<212> TYPE: DNA
<213> ORGANISM: Escherichia coli

<400> SEQUENCE: 6
ggggtacctt acaaactgca cg                                             22

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence:  N-terminal
      motif
<221> NAME/KEY: UNSURE
<222> LOCATION: (4)
<223> OTHER INFORMATION: Xaa at position 4 in this sequence is unknown
<221> NAME/KEY: UNSURE
<222> LOCATION: (6)
<223> OTHER INFORMATION: Xaa at position 6 in this sequence is unknown

<400> SEQUENCE: 7

Arg His Gly Xaa Arg Xaa Pro
  1               5
```

<210> SEQ ID NO 8
<211> LENGTH: 30
<212> TYPE: PRT
<213> ORGANISM: Escherichia coli

<400> SEQUENCE: 8

Met Trp Tyr Phe Leu Trp Phe Val Gly Ile Leu Leu Met Cys Ser Leu
 1               5                  10                  15

Ser Thr Leu Val Leu Val Trp Leu Asp Pro Arg Leu Lys Ser
                20                  25                  30

<210> SEQ ID NO 9
<211> LENGTH: 1489
<212> TYPE: DNA
<213> ORGANISM: Escherichia coli

<400> SEQUENCE: 9

| | | | | | | |
|---|---|---|---|---|---|---|
| taaggagcag | aaacaatgtg | gtatttcctt | tggttcgtcg | gcattttgtt | gatgtgttcg | 60 |
| ctctccaccc | ttgtgttggt | atggctggac | ccgcgattga | aaagttaacg | aacgtaagcc | 120 |
| tgatccggcg | cattagcgtc | gatcaggcaa | taatatcgga | tatcaaagcg | gaaacatatc | 180 |
| gatgaaagcg | atcttaatcc | cattttatc | tcttttgatt | ccgttaaccc | cgcaatctgc | 240 |
| attcgctcag | agtgagccgg | agctgaagct | ggaaagtgtg | gtgattgtca | gccgtcatgg | 300 |
| tgtgcgtgcc | ccaaccaagg | ccacgcaact | gatgcaggat | gtcacccag | acgcatggcc | 360 |
| aacctggccg | gtaaaactgg | gttggctgac | accacgcggt | ggtgagctaa | tcgcctatct | 420 |
| cggacattac | caacgccagc | gtctggtggc | cgacggattg | ctggcgaaaa | agggctgccc | 480 |
| gcagcctggt | caggtcgcga | ttattgctga | tgtcgacgag | cgtacccgta | aaacaggcga | 540 |
| agccttcgcc | gccgggctgg | cacctgactg | tgcaataacc | gtacataccc | aggcagatac | 600 |
| gtccagtccc | gatccgttat | ttaatcctct | aaaaactggc | gtttgccaac | tggataacgc | 660 |
| gaacgtgact | gacgcgatcc | tcagcagggc | aggagggtca | attgctgact | ttaccgggca | 720 |
| tcggcaaacg | gcgtttcgcg | aactggaacg | ggtgcttaat | ttttcccaat | aaacttgtg | 780 |
| ccttaaccgt | gagaaacagg | acgaaagctg | ttcattaacg | caggcattac | catcggaact | 840 |
| caaggtgagc | gccgacaatg | tttcattaac | cggtgcggta | agcctcgcat | caatgctgac | 900 |
| ggaaatattt | ctcctgcaac | aagcacaggg | aatgccggag | ccggggtggg | gaaggatcac | 960 |
| tgattcacac | cagtggaaca | ccttgctaag | tttgcataac | gcgcaatttt | atttactaca | 1020 |
| acgcacgcca | gaggttgccc | gcagtcgcgc | caccccgtta | ttggatttga | tcatggcagc | 1080 |
| gttgacgccc | catccaccgc | aaaaacaggc | gtatggtgtg | acattaccca | cttcagtgct | 1140 |
| gtttattgcc | ggacacgata | ctaatctggc | aaatctcggc | ggcgcactgg | agctcaactg | 1200 |
| gacgcttcca | ggtcagccgg | ataacacgcc | gccaggtggt | gaactggtgt | ttgaacgctg | 1260 |
| gcgtcggcta | agcgataaca | gccagtggat | tcaggtttcg | ctggtcttcc | agactttaca | 1320 |
| gcagatgcgt | gataaaacgc | cgctatcatt | aaatacgccg | cccggagagg | tgaaactgac | 1380 |
| cctggcagga | tgtgaagagc | gaaatgcgca | gggcatgtgt | tcgttggccg | gttttacgca | 1440 |
| aatcgtgaat | gaagcgcgca | taccggcgtg | cagtttgtaa | tggtacccc | | 1489 |